United States Patent
Hodgson et al.

(10) Patent No.: US 6,482,939 B1
(45) Date of Patent: Nov. 19, 2002

(54) FORM VI 5,6-DICHLORO-2-(ISOPROPYLAMINO)-1-(β-L-RIBOFURANOSYL)-1H-BEZIMIMIDAZOLE

(75) Inventors: Anne Hodgson, Dartford (GB); Lian-Feng Huang, Raleigh, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 60 days.

(21) Appl. No.: 09/647,868

(22) PCT Filed: Apr. 1, 1999

(86) PCT No.: PCT/EP99/02213

§ 371 (c)(1),
(2), (4) Date: Nov. 17, 2000

(87) PCT Pub. No.: WO99/51617

PCT Pub. Date: Oct. 14, 1999

(30) Foreign Application Priority Data

Apr. 7, 1998 (GB) ............................................. 9807355

(51) Int. Cl.[7] ...................... A61K 31/70; C07H 19/052
(52) U.S. Cl. ......................................... 536/28.9; 514/43
(58) Field of Search ............................. 514/43; 536/289

(56) References Cited

U.S. PATENT DOCUMENTS

| | | |
|---|---|---|
| 3,399,987 A | 9/1968 | Woods et al. |
| 3,555,040 A | 1/1971 | Frick et al. |
| 3,655,901 A | 4/1972 | Jensen et al. |
| 5,248,672 A | 9/1993 | Townsend et al. |
| 5,360,795 A | 11/1994 | Townsend et al. |
| 5,473,063 A | 12/1995 | Classon et al. |

(List continued on next page.)

FOREIGN PATENT DOCUMENTS

| | | |
|---|---|---|
| GB | 2319961 A | 6/1998 |
| WO | WO 9207867 | 5/1992 |
| WO | WO 9408456 | 4/1994 |
| WO | WO96 01833 | 1/1996 |
| WO | WO97/25337 | 7/1997 |
| WO | WO99/51618 | 10/1999 |

OTHER PUBLICATIONS

A. Graul, et al., "1263W94 Antiviral", *Drugs of the Future*, vol. 22, No. 7, pp. 707–710 (1997).

Gordon, Irving, et al., "Kinetics of Decay in the Expression of Interferon–Dependent MRNAs Responsible for Resistance to Virus", *Proc. National Academy Sciences USA*, vol. 77, No. 1, pp. 452–456 (1980).

Devivar, Rodrigo V., et al., "Benzimidazole Ribonucleosides: Observation of an Unexpected Nitration when Performing Non–Aqueous Diazotizations with t–butyl Nitrite, "*Bioorganic & Medicinal Chemistry Letters*, vol. 2, No. 9, (1992), pp. 1105–1110.

Tigges, Michael A., et al., "Human CD8+ Herpes Simplex Virus–Specific Cytotoxic T–Lymphocyte Clones Recognize Diverse Viron Protein Antigens", *Journal of Virology*, vol. 66, No. 3, (1992), 1622–34.

Devivar, Rodrigo V., et al., "Benzimidazole Ribonucleosides: Design, Synthesis, and Antiviral Activity of Certain 2–(Alkylthio)–and 2–(benzylthio)–5, 6–dichloro–1–(B–D–ribofuranosyl) benzimidazoles", *Journal of Medicinal Chemistry*, vol. 37, No. 18, (1994), pp. 2942–2949.

(List continued on next page.)

*Primary Examiner*—Samuel Barts
*Assistant Examiner*—Devesh Khare
(74) *Attorney, Agent, or Firm*—Lorie Ann Morgan

(57) ABSTRACT

The invention relates to Form VI 5,6-dichloro-2-(isopropylamino)-1-β-L-ribofuranosyl-1H-benzimidazole, pharmaceutical compositions comprising the same, and their use in medical therapy.

15 Claims, 10 Drawing Sheets

U.S. PATENT DOCUMENTS

| | | |
|---|---|---|
| 5,574,058 A | 11/1996 | Townsend et al. |
| 5,646,125 A | 7/1997 | Townsend et al. |
| 5,654,283 A | 8/1997 | Townsend et al. |
| 5,665,709 A | 9/1997 | Townsend et al. |
| 6,077,832 A * | 6/2000 | Chamberlain et al. ........ 514/43 |

OTHER PUBLICATIONS

Townsend, Leroy B., et al., "Design, Synthesis, and Antiviral Activity Activity of Certain 2,5, 6–Trihalo–1–(B–D–ribofuranosyl)benzimidazoles", *Journal of Medicinal Chemistry*, vol. 38, No. 20, (1995), 4098–4105.

Yankulov, Krassimir, et al., The Transcriptional Elongation Inhibitor 5,6–Dichloro–1–B–D–ribofuranosylbenzimidazole Inhibits Translation Factor HH–Associated Protein Kinase, *Journal of Biological Chemistry*, vol. 270, No. 41, (1995), pp. 23922–23925.

Nassiri, M. Reza, et al., "Comparison of Benzimidazole Nucleosides and Ganciclovir on the In Vitro Proliferation and Colony Formation of Human Bone Marrow Progenitor Cells," *British Journal of Haematology*, vol. 93, No. 2, (1996), pp. 273–279.

Gudmundsson, Kristjan S., et al., "Synthesis and Antiviral Activity of Certain 5'–Modified Analogs of 2,5, 6–Trichloro–1–(B–D–ribofuranosyl) benzimidazole," *Journal of Medicinal Chemistry*, vol. 40, No. 5, (1997), pp. 785–793.

Fessenden, Ralph J., et al., "Crystallization", *Organic Laboratory Techniques*, 3$^{rd}$ edition, Brooks/Cole (Canada), (2001), only preface and pp. 23–38.

Fieser, Louis D., et al., "Crystallization", *Organic Experiments*, DC Heath and Company, Boston, MA, (1964), only preface and pp. 41–51.

Zou, Ruiming, et al., "Design, Synthesis, and Antiviral Evaluation of 2–Chloro–5–6, dihalo–1–(B–D–ribofuranosyl) benzimidazoles as Potential Agents for Human Cytomegalovirus Infections", *Journal of Medicinal Chemistry*, vol. 40, No. 5, (1997), pp. 811–818.

* cited by examiner

TGA thermogram for form VI

Moisture sorption isotherm for form VI

FORM VI 5,6-DICHLORO-2-(ISOPROPYLAMINO)-1-(β-L-RIBOFURANOSYL)-1H-BEZIMIMIDAZOLE

This application is a Rule 371 Application of PCT/EP99/02213, filed Apr. 1, 1999, which claims priority to Great Britain Patent Application No. 9807355.4, filed Apr. 7, 1998.

BACKGROUND OF THE INVENTION

The present invention relates to a crystalline form of the antiviral compound 5,6-dichloro-2-(isopropylamino)-1-(β-L-ribofuranosyl)-1H-benzimidazole (also known as 1263W94; the compound of formula (I)), pharmaceutical formulations comprising this crystalline form of the antiviral compound, and their use in therapy.

5,6-Dichloro-2-(isopropylamino)-1-(β-L-ribofuranosyl)-1H-benzimidazole is a benzimidazole derivative useful in medical therapy. WO96/01833 discloses the compound of formula (I) and its use for the treatment or prophylaxis of viral infections such as those caused by herpes viruses. The compound as disclosed in WO96/01833 is in the form of an amorphous, non-crystalline material.

The structure of 5,6-dichloro-2-(isopropylamino)-1-(β-L-ribofuranosyl)-1H-benzimidazole, the compound of formula (I), is shown below:

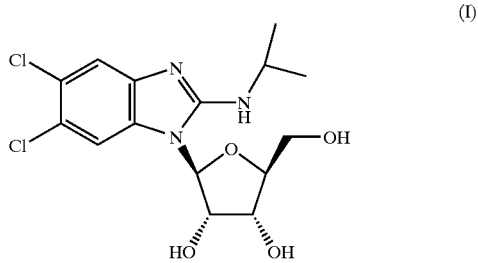

(I)

We have now found that the compound of formula (I) can exist in various crystalline forms and solvates. Moreover we have discovered a particular crystalline form of the compound of formula (I) Form VI, which is anhydrous and crystalline and which surprisingly has particularly good pharmaceutical properties. Form VI is the most thermodynamically stable form of the compound of formula (I). It may be easily prepared and may be manufactured on a commercial scale. It is particularly stable and essentially non-hygroscopic. Batches of this crystalline form can be consistently made to a high crystal form purity i.e. where the proportion of other amorphous and crystalline forms of the compound of formula (I) is limited. Furthermore this anhydrous crystalline form has good storage properties and can be readily formulated into pharmaceutical compositions such as tablets and capsules. The crystalline forms and solvates of the compound of formula (I) may be characterized by their X-ray powder diffraction patterns.

DETAILED DESCRIPTION OF THE INVENTION

According to a first aspect of the invention there is provided the compound of formula (I) in a thermodynamically stable crystalline form (hereinafter referred to as Form VI). Form VI is defined by the X-ray powder diffraction pattern illustrated in FIG. 6, which is obtained by a properly aligned diffractometer equipped with a diffracted beam graphite monochromator using copper Kα X-radiation. Form VI may be prepared from the ethanol solvate of the compound of formula (I) at certain relative humidities. Form VI may also be prepared from seeding slurries of Form II or ethanol solvate in water with Form VI. Other solvent systems that may yield Form VI on seeding include ethyl acetate/toluene, isopropanol/toluene, 2-butanone/toluene.

In a further aspect of the invention, there is provided the compound of formula (I) as a mixture of Form VI with any one or more of Forms I, II, IV, V or solvates or as a mixture of Form VI and amorphous material, or as a mixture of Form VI, amorphous material and one or more other crystalline forms or solvates.

As used herein, the term "solvate" is a complex of variable stoichiometry formed by a solute (a compound of formula (I)) and a solvent. Solvents, by way of example, include water, methanol, ethanol, or acetic acid. Hereinafter, reference to a compound of formula (I) is to the amorphous form of that compound, unless another form or solvate thereof is specified.

Figure 6:
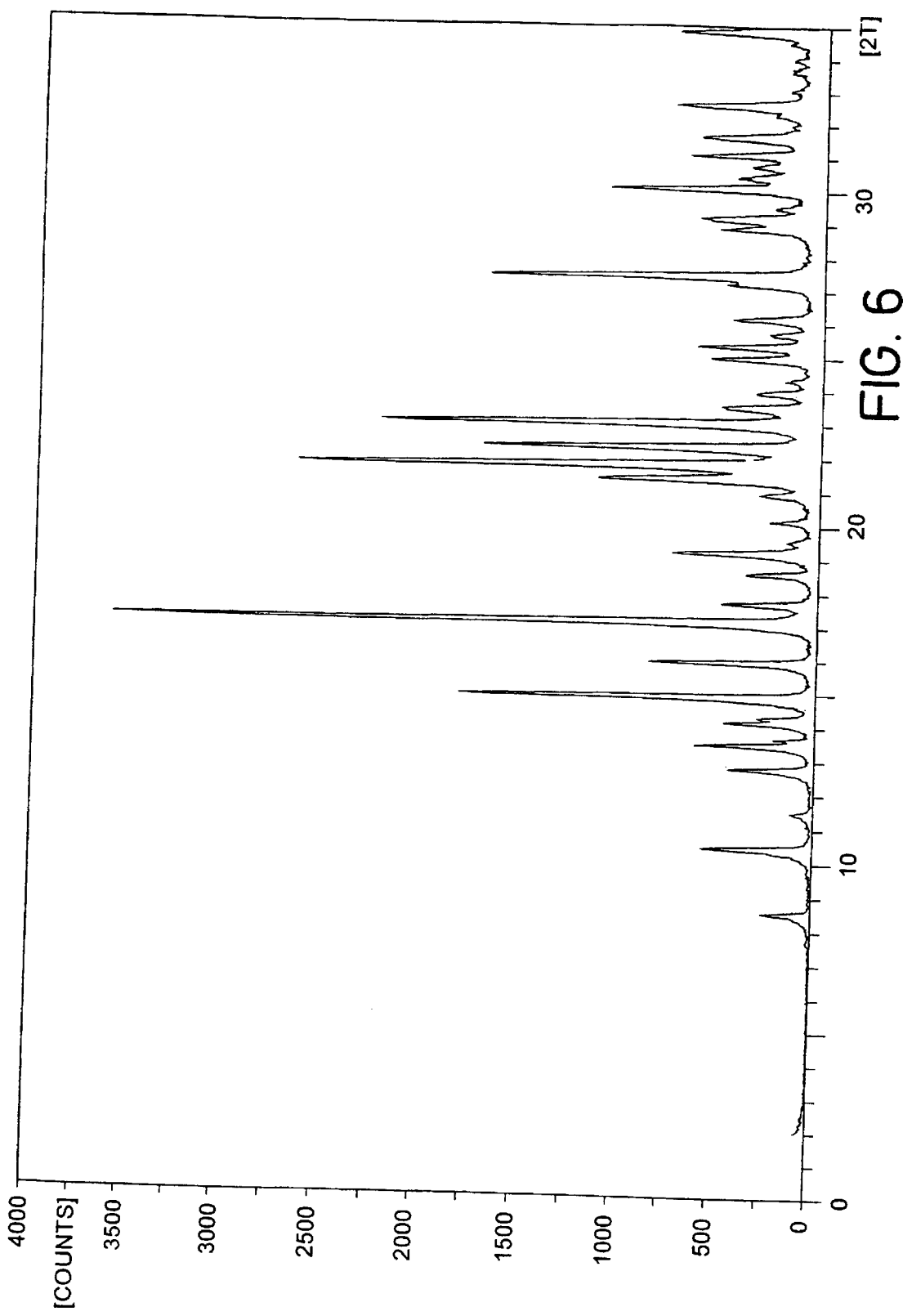
FIG. 6. X-ray powder diffraction pattern of Form VI of the compound of formula (I). This pattern was obtained in accordance with the procedures set forth in Example 22.

Hereinafter by "anhydrous crystalline form" according to the invention, we mean a crystalline form having substantially the same X-ray powder diffraction pattern as shown in FIG. 6 when measured with a properly aligned diffractometer equipped with a diffracted beam graphite monochromator using copper Kα X-radiation.

The X-ray powder diffraction pattern of the anhydrous crystalline Form VI of the present invention is determined using conventional techniques and equipment known to those skilled in the art of physical characterization. The diffraction patterns of FIGS. 1–6 were obtained with a Philips X-Pert MPD diffractometer system equipped with a diffracted beam graphite monochromator using copper Kα

X-radiation and an automated divergent slit. A xenon proportional counter was used as the detector. The powder sample used to generate the X-ray powder diffraction data was prepared by conventional back filled sample preparation techniques using a 16 mm diameter holder about 2.0 mm thick.

A powder sample of each of Forms I, II, IV, V, VI, and the ethanolate were used to produce the X-ray powder diffraction patterns of FIGS. 1, 2, 4, 5, 6, and 3, respectively. The X-ray diffraction patterns for each of the various forms and solvates are unique to the particular form. Each crystalline anhydrous form or solvate exhibits a diffraction pattern with a unique set of diffraction peaks which can be expressed in 2 theta angles (°), d-spacings (Å) and/or relative peak intensities.

2 Theta diffraction angles and corresponding d-spacing values account for positions of various peaks in the X-ray diffraction pattern. D-spacing values are calculated with observed 2 theta angles and copper Kα1 wavelength using the Bragg equation. Slight variations in observed 2 theta angles and d-spacings are expected based on the specific diffractometer employed and the analyst's sample preparation technique.

More variation is expected for the relative peak intensities. Identification of the exact crystal form of a compound should be based primarily on observed 2 theta angles or d-spacings with lesser importance place on relative peak intensities. To identify 5,6-dichloro-2-(isopropylamino)-1-(β-L-ribofuranosyl)-1H-benzimidazole Form VI, the single most characteristic 2 theta angle peak occurs at 8.53 degrees, or 10.36 Å d-spacing.

Although one skilled in the art can identify Form VI from the characteristic 2 theta angle peak at 8.53 degrees, in some circumstances it may be desirable to rely upon multiple 2 theta angles or multiple d-spacings for the identification of Form VI. 5,6-Dichloro-2-(isopropylamino)-1-(β-L-ribofuranosyl)-1H-benzimidazole Form VI can also be identified by the presence of multiple characteristic 2 theta angle peaks including two, three, four, five, six, seven, eight, nine, ten or all eleven of the 2 theta angles which are reasonably characteristic of this particular crystalline form. These peaks occur at the following positions, expressed in 2 theta angles: 8.53, 10.47, 13.51, 14.95, 15.98, 17.23, 21.41, 21.83, 22.35, 23.07, and 27.49 degrees. In one embodiment at least five of the foregoing 2 theta angles are employed to identify Form VI. The crystalline anhydrous Form VI typically exhibits 2 theta angle peaks in addition to the foregoing peaks. For example, Form VI may exhibit 2 theta angle peaks at essentially the following positions: 8.5, 10.5, 12.8, 13.5, 14.2, 15.0, 16.0, 17.2, 17.8, 19.2, 21.4, 21.8, 22.4, 23.1, 25.0, 25.4, 27.5, 29.2, 30.1, 31.1, and 32.6 degrees.

Some margin of error is present in each of the 2 theta angle assignments and d-spacings reported above. The error in determining d-spacings decreases with increasing diffraction scan angle or decreasing d-spacing. The margin of error in the foregoing 2 theta angles is approximately ±0.05 degrees for each of the foregoing peak assignments. The margin of error in d-spacing values is approximately ±0.05 Angstroms.

Since some margin of error is possible in the assignment of 2 theta angles and d-spacings, the preferred method of comparing X-ray powder diffraction patterns in order to identify a particular crystalline form is to overlay the X-ray powder diffraction pattern of the unknown form over the X-ray powder diffraction pattern of a known form. For example, one skilled in the art can overlay an X-ray powder diffraction pattern of an unidentified crystalline form of 5,6-dichloro-2-(isopropylamino)-1-(β-L-ribofuranosyl)-1H-benzimidazole, obtained using the methods described herein, over FIG. 6 and readily determine whether the X-ray diffraction pattern of the unidentified form is substantially the same as the X-ray powder diffraction pattern of Form VI. If the X-ray powder diffraction pattern is substantially the same as FIG. 6, the previously unknown crystalline form can be readily and accurately identified as Form VI. The same technique can be used to determine if the unidentified crystalline form is any of Forms I, II, IV, V, or the ethanolate by overlaying the X-ray powder diffraction pattern over FIGS. 1, 2, 4, 5, or 3 respectively.

Although 2 theta angles or d-spacings are the primary method of identifying a particular crystalline form, it may be desirable to also compare relative peak intensities. As noted above, relative peak intensities may vary depending upon the specific diffractometer employed and the analyst's sample preparation technique. The peak intensities are reported as intensities relative to the peak intensity of the strongest peak. The intensity units on the X-ray diffraction plot are counts/sec. The absolute counts=counts/time×count time=counts/sec×10 sec. Considering 2 theta angles, d-spacing (Å) and relative peak intensity (I), Form VI 5,6-dichloro-2-(isopropylamino)-1-(β-L-ribofuranosyl)-1H-benzimidazole exhibits the following X-ray diffracation pattern characteristics:

| | Form VI | |
|---|---|---|
| 2 theta angle (°)[1] | Å[2] | I |
| 8.53 | 10.36 | 14.5 |
| 10.47 | 8.45 | 25.6 |
| 12.80 | 6.91 | 16.8 |
| 14.16 | 6.25 | 16.4 |
| 13.51 | 6.55 | 21.4 |
| 14.95 | 5.92 | 60.4 |
| 15.98 | 5.54 | 26.2 |
| 17.23 | 5.14 | 100.0 |
| 19.25 | 4.61 | 19.3 |
| 21.41 | 4.15 | 26.5 |
| 21.83 | 4.07 | 60.4 |
| 22.35 | 3.97 | 38.3 |
| 23.07 | 3.85 | 48.7 |
| 27.49 | 3.24 | 30.9 |
| 30.11 | 2.97 | 18.5 |

[1]Margin of error = approx. ±0.05 degrees.
[2]Margin of error = approx. ±0.05 Angstoms.

Based upon the foregoing characteristic features of the X-ray powder diffraction pattern of Form VI, one skilled in the art can readily identify Form VI 5,6-dichloro-2-(isopropylamino)-1-(β-L-ribofuranosyl)-1H-benzimidazole. It will be appreciated by those skilled in the art that the X-ray powder diffraction pattern of a sample of Form VI, obtained using the methods described herein, may exhibit additional peaks. The foregoing and following tables provide the fifteen most intense peaks which are characteristic of that particular crystalline form or solvate. The tables should not be interpreted as an exhaustive list of peaks exhibited by the particular form or solvate.

In contrast to the foregoing X-ray powder diffraction characteristics of Form VI, Forms I, II, IV, V and the ethanolate each exhibit distinct 2 theta angles, d-spacings and relative intensities, which can be used to differentiate each of these forms from Form VI and from each other. Forms I, II, IV, V and the ethanolate are defined by their X-ray powder diffraction pattern, obtained with a properly aligned diffractometer equipped with a diffracted beam graphite monochromator using copper Kα X-radiation; patterns are provided in FIGS. 1, 2, 4, 5, and 3, respectively.

Form I 5,6-dichloro-2-(isopropylamino)-1-(β-L-ribofuranosyl)-1H-benzimidazole is further characterized by the following 2 theta angles, d-spacings, and relative peak intensities, obtained by the method of Example 22 below.

| Form I | | |
|---|---|---|
| 2 theta angle (°)[1] | Å[1] | I |
| 7.90 | 11.19 | 58.8 |
| 10.39 | 8.51 | 49.7 |
| 14.63 | 6.05 | 33.3 |
| 15.79 | 5.61 | 46.1 |
| 16.95 | 5.23 | 16.4 |
| 19.24 | 4.61 | 14.4 |
| 20.75 | 4.28 | 29.4 |
| 21.99 | 4.04 | 21.0 |
| 22.77 | 3.90 | 100.0 |
| 24.14 | 3.68 | 35.2 |
| 24.71 | 3.60 | 20.5 |
| 25.72 | 3.46 | 13.9 |
| 25.97 | 3.43 | 43.2 |
| 29.44 | 3.03 | 13.9 |
| 31.09 | 2.87 | 14.7 |

[1]Margin of error = approx. ±0.05

Form II 5,6-dichloro-2-(isopropylamino)-1-(β-L-ribofuranosyl)-1H-benzimidazole is further characterized by the following 2 theta angles, d-spacings, and relative peak intensities, obtained by the method of Example 22 below.

| Form II | | |
|---|---|---|
| 2 theta angle (°)[1] | Å[2] | I |
| 7.91 | 11.17 | 100.0 |
| 10.86 | 8.14 | 10.1 |
| 12.69 | 6.97 | 5.2 |
| 13.65 | 6.48 | 4.7 |
| 14.94 | 5.93 | 8.4 |
| 16.11 | 5.50 | 12.8 |
| 17.33 | 5.11 | 17.5 |
| 18.23 | 4.86 | 18.2 |
| 19.60 | 4.53 | 19.6 |
| 21.88 | 4.06 | 18.8 |
| 23.24 | 3.82 | 19.0 |
| 23.92 | 3.72 | 26.7 |
| 25.27 | 3.52 | 24.5 |
| 27.70 | 3.22 | 34.9 |
| 29.21 | 3.06 | 14.2 |

[1]Margin of error = approx. ±0.09

Form II may also exhibit peaks at essentially the following 2 theta angles: 7.9, 10.9, 16.1, 17.3, 18.2, 19.6, 21.9, 23.9 degrees.

The ethanolate of 5,6-dichloro-2-(isopropylamino)-1-(β-L-ribofuranosyl)-1H-benzimidazole is further characterized by the following 2 theta angles, d-spacings, and relative peak intensities, obtained by the method of Example 22 below.

| Ethanolate | | |
|---|---|---|
| 2 theta angle (°)[1] | Å[2] | I |
| 9.07 | 9.74 | 45.2 |
| 10.38 | 8.52 | 22.7 |
| 15.95 | 5.55 | 40.4 |
| 17.72 | 5.00 | 100.0 |
| 18.96 | 4.68 | 17.2 |
| 19.79 | 4.48 | 18.4 |
| 20.75 | 4.28 | 30.4 |
| 21.37 | 4.16 | 27.7 |
| 21.89 | 4.06 | 19.0 |
| 22.08 | 4.02 | 17.5 |
| 22.96 | 3.87 | 40.6 |
| 23.93 | 3.72 | 41.3 |
| 25.40 | 3.50 | 26.7 |
| 27.65 | 3.22 | 19.8 |
| 29.05 | 3.07 | 25.4 |

[1]Margin of error = approx. ±0.05

The ethanolate may also exhibit peaks at essentially the following 2 theta angles: 6.6, 9.1, 9.4, 10.4, 11.0, 14.7, 16.0, 17.2, 17.7, 18.3, 20.8, 21.4, 23.0, 23.9, 25.4, 27.7, 29.1 degrees.

Form IV 5,6-dichloro-2-(isopropylamino)-1-(β-L-ribofuranosyl)-1H-benzimidazole is further characterized by the following 2 theta angles, d-spacings, and relative peak intensities, obtained by the method of Example 22 below.

| Form IV | | |
|---|---|---|
| 2 theta angle (°)[1] | Å[1] | I |
| 9.29 | 9.51 | 15.6 |
| 11.78 | 7.51 | 12.5 |
| 16.04 | 5.52 | 20.1 |
| 18.67 | 4.75 | 25.1 |
| 19.54 | 4.54 | 11.5 |
| 22.06 | 4.03 | 100.0 |
| 22.39 | 3.97 | 11.6 |
| 22.68 | 3.92 | 17.9 |
| 23.34 | 3.81 | 15.5 |
| 23.68 | 3.75 | 10.0 |
| 24.40 | 3.65 | 28.7 |
| 28.72 | 3.11 | 11.1 |
| 29.64 | 3.01 | 13.0 |
| 30.92 | 2.89 | 26.5 |
| 31.62 | 2.83 | 13.9 |

[1]Margin of error = approx. ±0.05

Form IV may also exhibit peaks at essentially the following 2 theta angles: 7.5, 9.3, 11.8, 16.0, 18.7, 19.4, 19.5, 22.1, 22.7, 24.4, 29.6, 30.9 degrees.

Form V 5,6-dichloro-2-(isopropylamino)-1-(β-L-ribofuranosyl)-1H-benzimidazole is further characterized by the following 2 theta angles, d-spacings, and relative peak intensities, obtained by the method of Example 22 below.

| Form V | | |
|---|---|---|
| 2 theta angle (°)[1] | Å[1] | I |
| 9.07 | 9.75 | 19.1 |
| 9.35 | 9.46 | 14.3 |
| 10.74 | 8.23 | 14.0 |
| 13.30 | 6.65 | 26.1 |
| 17.04 | 5.20 | 18.5 |

-continued

| Form V | | |
|---|---|---|
| 2 theta angle (°)[1] | Å[1] | I |
| 18.13 | 4.89 | 39.2 |
| 18.78 | 4.72 | 57.0 |
| 20.41 | 4.35 | 39.5 |
| 21.75 | 4.08 | 100.0 |
| 22.71 | 3.91 | 15.8 |
| 23.02 | 3.86 | 20.3 |
| 26.87 | 3.32 | 23.4 |
| 28.34 | 3.15 | 24.7 |
| 28.55 | 3.12 | 51.1 |
| 30.22 | 2.95 | 39.0 |

[1]Margin of error = approx. ±0.05

Form V may also exhibit peaks at essentially the following 2 theta angles: 9.1, 9.3, 10.7, 13.3, 17.0, 18.1, 18.8, 20.4, 21.8, 26.9, 28.6, 30.2 degrees.

Other methods of physical characterization can also be employed to identify the anhydrous crystalline Form VI of the present invention. Examples of suitable techniques which are known to those skilled in the art to be useful for the physical characterization or identification of a crystalline form or solvate include but are not limited to melting point, differential scanning calorimetry, and infrared absorption spectra. These techniques may be employed alone or in combination to characterize a given anhydrous crystalline form or solvate.

The invention relates to the anhydrous crystalline form VI both in pure form and in admixture with other forms of the compound of formula (I). For example, Form VI may be in admixture with any one or more of Forms I, II, IV, V, or the ethanolate. Alternatively Form VI may be in admixture with amorphous compound of formula (I). In another embodiment, Form VI is in admixture with both amorphous compound of formula (I) and one or more other crystalline forms or solvates including Forms I, II, IV, V and the ethanolate.

The present invention expressly contemplates the foregoing mixtures of Form VI with one or more of the amorphous compound of formula (I), and/or other crystalline anhydrous forms and solvates. It should be understood that admixtures of Form VI with amorphous compound of formula (I) and/or other crystalline forms or solvates may result in the masking or absence of one or more of the foregoing X-ray powder diffraction peaks described above for Form VI. Methods are known in the art for analyzing such admixtures of crystalline forms in order to provide for the accurate identification of the presence or absence of particular crystalline forms in the admixture.

In addition to the foregoing forms, Form VI may also be in admixture with hydrated crystalline forms. For example in any batch containing the anhydrous crystalline compound of formula (I) Form VI, there may also be hydrated crystalline Form VI. Since the anhydrous crystalline form of the compound of formula (I) Form VI is essentially free of water of hydration, the proportion of hydrate forms of the compound of formula (I) Form VI in any batch of the compound may be measured by the overall water of hydration content of each batch.

Figure 7:
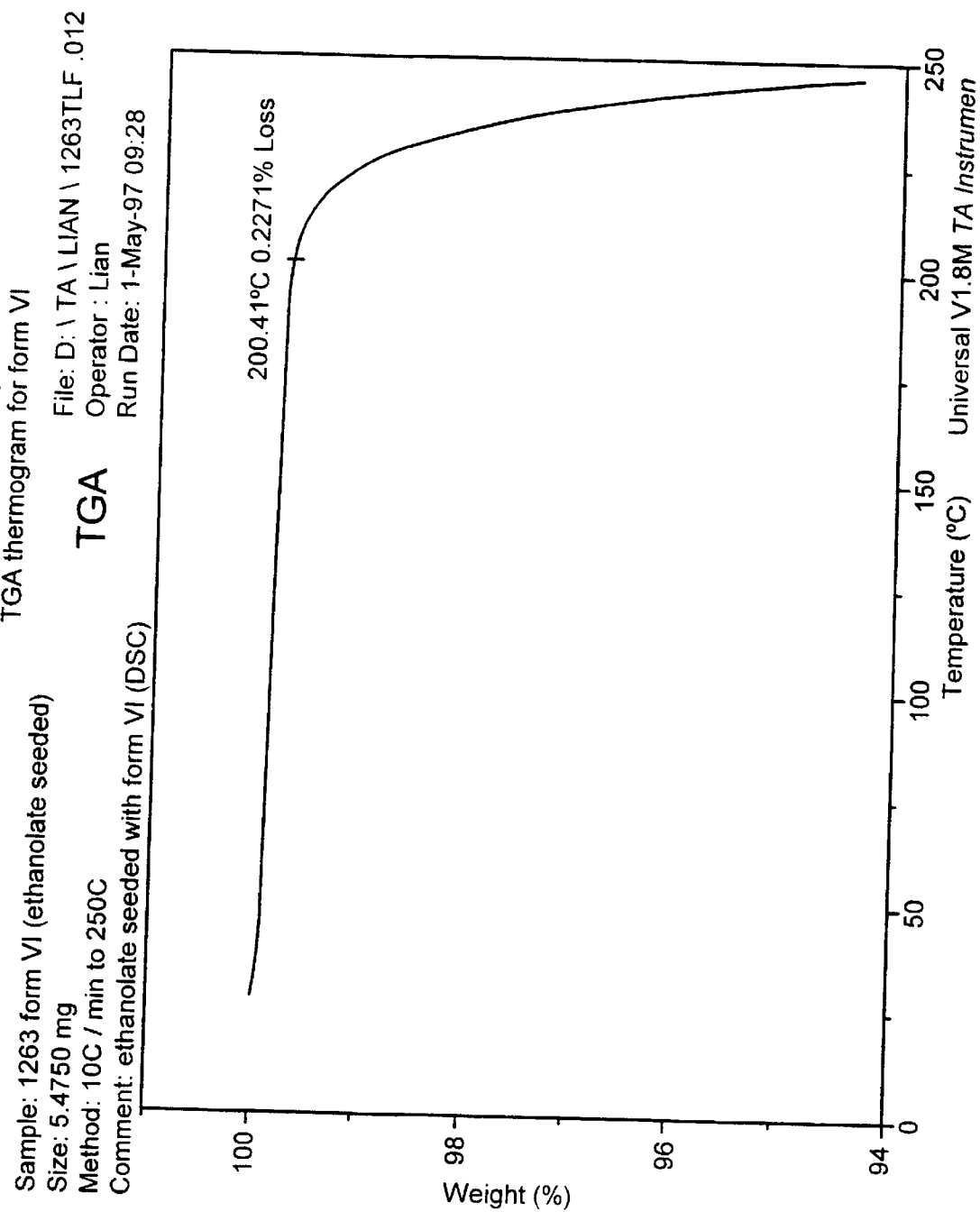
FIG. 7. TGA thermogram for Form VI of the compound of formula (I). This TGA thermogram was obtained in accordance with the procedures set forth in Example 22.

Accordingly, in a second aspect of the present invention there is provided the compound of formula (I) form VI, having a total volatile content of not more than 0.3% by weight (w/w) as determined by a TA Instruments Hi-Res TGA 2950 thermogravimetric analyzer (FIG. 7).

Figure 8:
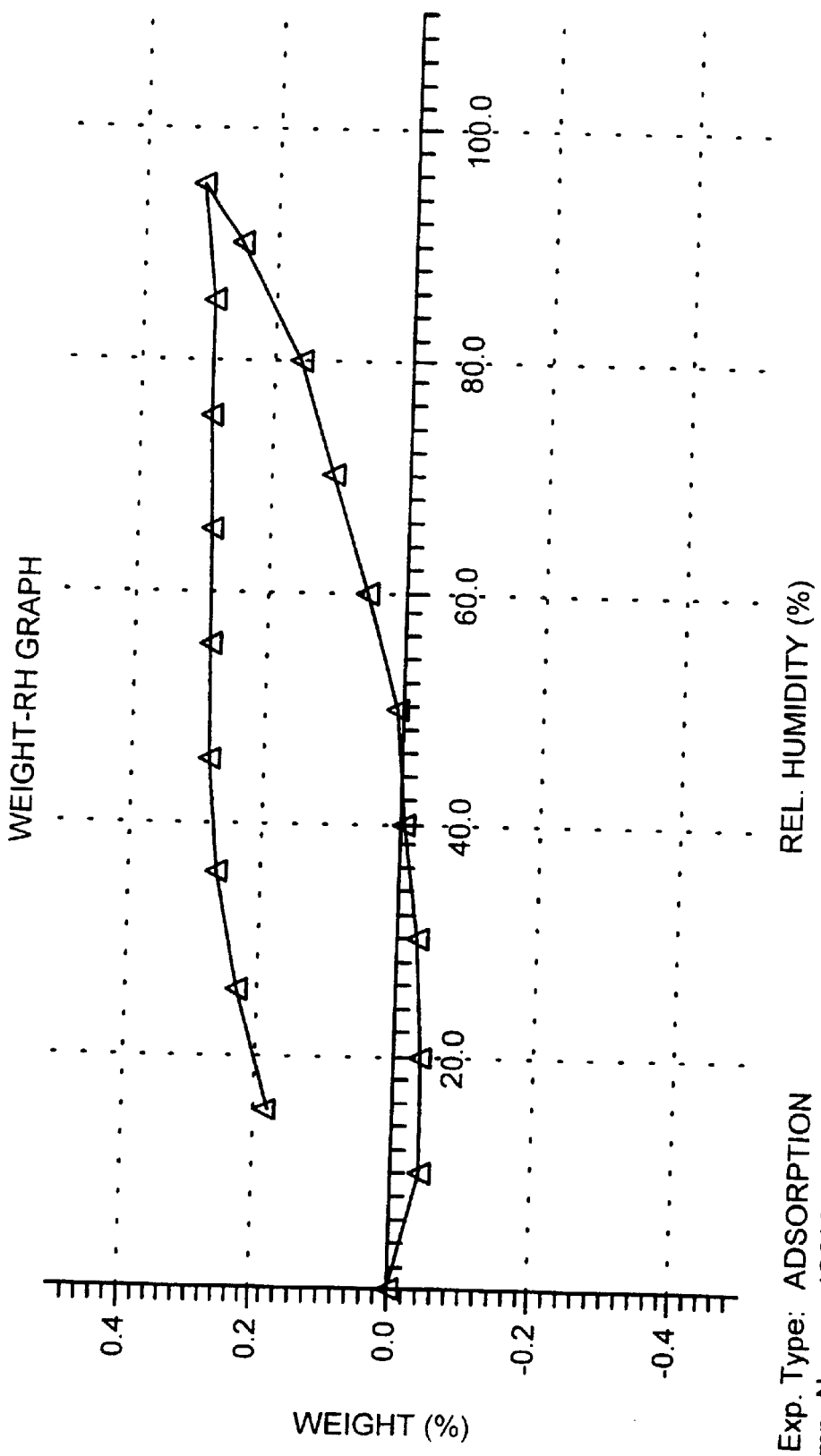
FIG. 8. Moisture sorption isotherm for Form VI of the compound of formula (I).

Gravimetric water vapor sorption showed that Form VI only absorbed 0.3% water when equilibrated up to 95% relative humidity at ambient temperature (FIG. 8).

According to a further aspect, the present invention provides a process for the production of the compound of formula (I) in anhydrous crystalline Form VI which comprises treating the compound of formula (I) with a solubilising solvent serving to convert an amount of the compound of formula (I) into the anhydrous crystalline form VI.

The invention also provides a process for the production of the compound of formula (I) Form VI. The process comprises the steps of:
 a) forming or providing the compound of formula (I) in solution either in free base or salt form;
 b) isolating the compound of formula (I) from the solution and optionally removing unbound (damp, non-solvated) solvent leaving the compound of formula (I) in substantially dry form;
 c) treating the compound of formula (I) with a solubilising solvent serving to convert an amount of the optionally dried compound of formula (I) from step b) into anhydrous crystalline Form VI; and
 d) isolating the anhydrous crystalline form VI.

In one embodiment of the present invention, the compound of formula (I) Form VI, is prepared by recrystallization from ethyl acetate/toluene. According to this process, compound of formula (I) is treated with a solubilising solvent comprising ethyl acetate and toluene to convert the compound of formula (I) into anhydrous crystalline Form VI and the anhydrous crystalline Form VI is isolated from the solution, such as by removal of the solubilising solvent for example, by evaporation or drying. The compound of formula (I) may be in either the free base or the salt form.

The compound of formula (I) may be prepared by any method known in the art, but preferably by the methods described in WO 96/01833, incorporated herein by reference in its entirety.

The synthesis of the compound of formula (I) generally leads to the formation of the compound in solution in the reaction mixture from which it may be separated and purified as a solid product. The compound of formula (I) may then optionally be dried. A number of factors influence the crystalline form of the solid product and in accordance with the present invention the conditions of separation and/or subsequent processing are adjusted to produce the compound of formula (I) as the anhydrous crystalline form VI or as a mixture of Form VI with one or more other anhydrous crystalline forms or solvates and/or amorphous material. For example a hydrate form of the compound of formula (I) can be converted to the anhydrous crystalline form using a suitable solvent under appropriate conditions.

Such suitable solvent which is preferably a water-soluble organic solvent, should be sufficiently solubilising and be employed in an amount to allow partial solubilization to effect the conversion and precipitation for example from one anhydrous crystalline form to the desired anhydrous crystalline form of the compound of formula (I). Advantageously the solvent is eventually removed by drying under vacuum.

The damp compound of formula (I) following the first isolation (as in step b above) is preferably dried for example at about 30° C. to about 70° C. to provide substantially dry compound of formula (I).

The present invention also provides the compound of formula (I) Form VI for use in medical therapy, e.g. in the treatment or prophylaxis of a viral disease in an animal, e.g. a mammal such as a human. The compound is especially useful for the treatment or prophylaxis, including suppression of recurrence of viral diseases, such as herpes virus infections, for example, CMV infections, as well as disease caused by hepatitis B and hepatitis C viruses.

In addition to its use in human medical therapy, the compound of formula (I) Form VI may be administered to other animals for treatment or prophylaxis of viral diseases, e.g. to other mammals.

The present invention also provides a method for the treatment or prophylaxis, including suppression of recurrence, of a viral infection, particularly a herpes infection, CMV infection, or disease caused by hepatitis B or hepatitis C viruses in an animal, e.g. a mammal such as a human, which comprises administering to the animal an effective antiviral amount of the compound of formula (I) Form VI.

The present invention also provides the use of the compound of formula (I) Form VI in the preparation of a medicament for the treatment or prophylaxis of a viral infection.

The compound of formula (I) Form VI may be administered by any route appropriate to the condition to be treated, but generally the preferred route of administration is oral. It will be appreciated however, that the preferred route may vary with for example the condition of the recipient.

For each of the above-indicated utilities and indications the amounts required of the active ingredient (as above defined) will depend upon a number of factors including the severity of the condition to be treated and the identity of the recipient and will ultimately be at the discretion of the attendant physician or veterinarian. In general however, for each of these utilities and indications, a suitable effective dose will be in the range of 0.01 to 250 mg per kilogram body weight of recipient per day, advantageously in the range of 0.1 to 100 mg per kilogram body weight per day, preferably in the range of 0.5 to 30 mg per kilogram body weight per day, particularly 1.0 to 30 mg per kilogram body weight per day (unless otherwise indicated, all weights of the active ingredient are calculated with respect to the free base of the compound of formula (I)). The desired dose is preferably presented as one, two, three or four or more subdoses administered at appropriate intervals throughout the day. These sub-doses may be administered in unit dosage forms, for example, containing about 10 to 1200 mg, or 50 to 500 mg, preferably about 20 to 500 mg, and most preferably 100 to 400 mg of active ingredient per unit dose form.

While it is possible for the active ingredient to be administered alone, it is preferable to present it as a pharmaceutical formulation. The formulation comprises the active ingredient as above defined, together with one or more pharmaceutically acceptable excipients therefor and optionally other therapeutic ingredients. The excipient(s) must be "acceptable" in the sense of being compatible with the other ingredients of the formulation and not deleterious to the recipient thereof.

The formulations include those suitable for oral administration and may conveniently be presented in unit dosage form prepared by any of the methods well known in the art of pharmacy. Such methods include the step of bringing into association the active ingredient with the carrier which constitutes one or more accessory ingredients. In general, the formulations are prepared by uniformly and intimately bringing in to association the active ingredient with liquid carriers or finely divided solid carriers or both, and then, if necessary, shaping the product.

Formulations of the present invention suitable for oral administration may be presented as discrete units such as capsules, cachets, sachets of granules or tablets (such as a swallowable, dispersible or chewable tablet) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored any may be formulated so as to provide slow or controlled release of the active ingredient therein.

In addition to the oral dosage forms described hereinabove, the anhydrous crystalline form VI of the present invention may also be formulated for administration by topical, parenteral, and other administration routes using the carriers and techniques described in WO96/01833. It will be appreciated by those skilled in the art that the preparation of dosage forms as solutions of the anhydrous crystalline form VI substantially completely dissolved in a solvent, e.g., for parenteral administration, will preclude the identification of the particular crystalline form utilized in the preparation of the solution. Nevertheless, anhydrous crystalline form VI can conveniently be used for the preparation of solutions by substantially completely solubilizing the crystalline form or solvate in a suitable solvent.

Preferred unit dosage formulations are those containing a daily dose or unit daily subdose (as herein above recited) or an appropriate fraction thereof, of the active ingredient.

It should be understood that in addition to the ingredients particularly mentioned above, the formulation of this invention may include other agents conventional in the art having regard to the type of formulation in question, for example those suitable for oral administration may include flavoring agents or taste masking agents.

The following examples are intended for illustration only and are not intended to limit the scope of the invention in any way.

EXAMPLE 1

5,6,-Dichloro-2-(isopropylamino)-1-β-L-ribofuranosyl-1H-benzimidazole Form I

The compound of formula (I) (200 mg) was placed in a Thermal Activity Monitor (TAM) and a few drops of water were added to make the powder wet. The vial was sealed and placed in a TAM chamber at 50° C. The mixture was cooled to ambient temperature and filtered. The damp residue was dried in vacuo at 60° C. overnight to give the compound of formula (I) Form I.

Figure 1:
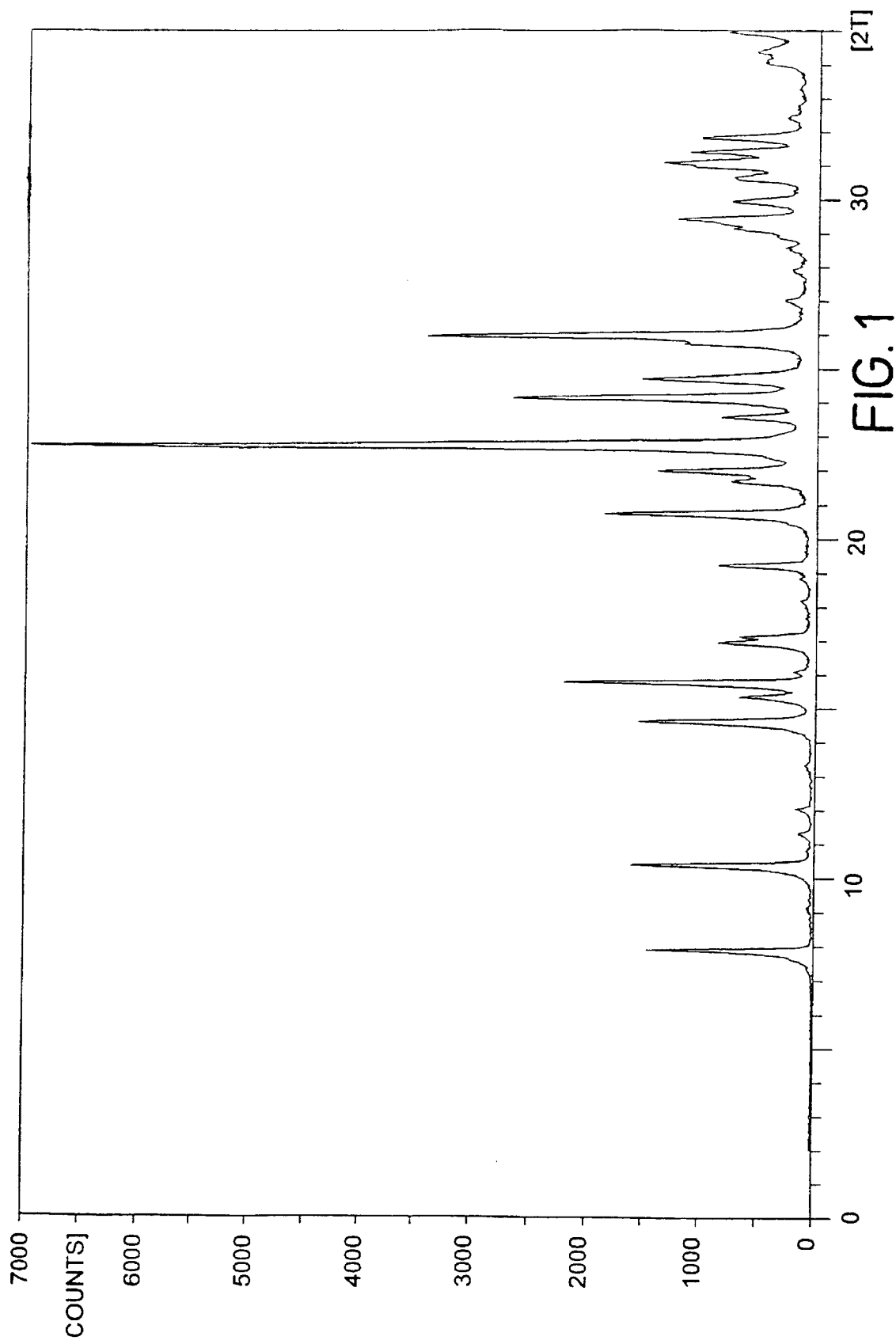
FIG. 1. X-ray powder diffraction pattern of Form I of the compound of formula (I). This pattern was obtained in accordance with the procedures set forth in Example 22.

The X-ray powder diffraction pattern of the product of Example 1 is shown in FIG. 1.

EXAMPLE 2

5,6,-Dichloro-2-(isopropylamino)-1-β-L-ribofuranosyl-1H-benzimidazole Form I

The compound of formula (I) (1.5 g) was suspended in water (30 ml) and heated to 65° C. with stirring. After approximately 0.5 h, stirring became difficult as a gum formed. After further heating, the gum turned solid and was broken up with a spatula. The mixture was heated at 65–70° C. for 9 h. The mixture was cooled to 20° C. and the solid collected by filtration and dried in vacuo at 40° C. for 24 h to give the compound of formula (I) Form I.

The X-ray powder diffraction pattern of the product of Example 2 is shown in FIG. 1.

EXAMPLE 3

5,6,-Dichloro-2-(isopropylamino)-1-β-L-ribofuranosyl-1H-benzimidazole Form I

The compound of formula (I) (5 g) and water (1.5 ml) were stirred and heated in an oil bath at 80° C. The powder turned to a gum and stirring ceased. Heating was continued for 8 h. The solid was loosened with a spatula and stirred occasionally. After cooling to 20° C., the solid was collected and dried in vacuo at 40° C. for 4 h.

The X-ray powder diffraction pattern of the product of Example 3 is shown in FIG. 1.

EXAMPLE 4

5,6,-Dichloro-2-(isopropylamino)-1-β-L-ribofuranosyl-1H-benzimidazole Form I

The compound of formula (I) (2 g) in toluene (15 ml) was heated at reflux for 19 h. On heating the suspension turned to a gum that solidified on further heating. The solid was collected by filtration and dried in vacuo at 40° C. to yield the compound of formula (I).

The X-ray powder diffraction pattern of the product of Example 4 is shown in FIG. 1.

EXAMPLE 5

Preparation of 5,6,-Dichloro-2-(isopropylamino)-1-β-L-ribofuranosyl-1H-benzimidazole Form I from Form II The compound of formula (I) Form II (2 g) in toluene (10 ml, 5 vol) was heated to 60° C., at which point the solid began to stick to the sides of the flask. On continued heating to 95° C., an oil formed. Heating was continued to 105° C., then toluene (2.5 vol) was added and heating continued. Reflux was continued for 3 h with rapid stirring. The oil bath temperature was reduced to 80° C. (internal temperature 73° C.) and heating continued for 3 h again with rapid stirring. The mixture was heated to reflux again for 16 h and then allowed to cool to room temperature. The loose solid was collected by filtration washing with toluene (2×5 ml) and dried in vacuo at 20° C. and at 40° C. in vacuo to yield a white solid. The residual solid was removed from the flask, collected by filtration, and dried in vacuo at 20° C. The filtrate was concentrated under reduced pressure to yield a solid.

The X-ray powder diffraction pattern of the product of Example 5 is shown in FIG. 1.

EXAMPLE 6

Preparation of 5,6,-Dichloro-2-(isopropylamino)-1-β-L-ribofuranosyl-1H-benzimidazole Form I from Form II The compound of formula (I) Form II (5 g) was stirred with water (1.5 ml) in an oil bath at 80° C. When the temperature of the oil bath reached about 60° C., the mixture became difficult to stir. Heating continued for 8 h with occasional stirring and then cooled to room temperature. The material was dried in vacuo at 40° C. for 4 h.

The X-ray powder diffraction pattern of the product of Example 6 is shown in FIG. 1.

EXAMPLE 7

5,6,-Dichloro-2-(isopropylamino)-1-β-L-ribofuranosyl-1H-benzimidazole Form II

The compound of formula (I) (100 g) was added to stirred toluene/methanol (4:1, 440 ml) and heated to 65° C. to give a clear solution. The solution was clarified through a filter with a line wash (toluene/methanol [4:1, 110 ml, warm]). The solution was heated back to 65° C. and toluene (4.5 vol) was added slowly, maintaining internal temperature above 65° C. When the addition was complete, the solution was cooled to 40° C. over 1 h and aged at 40° C. After 0.5 h, the mixture was seeded with the compound of formula (I) Form II and then aged for a further 4.5 h. The suspension was cooled to 20° C. over 1 h and aged at 20° C. for 12 h and then cooled to 5° C. over 1 h and aged for 3 h. The solid was collected by filtration, washing with toluene (2×100 ml). The wet cake was transferred to a dryer and dried in vacuo at 20° C.

Figure 2:
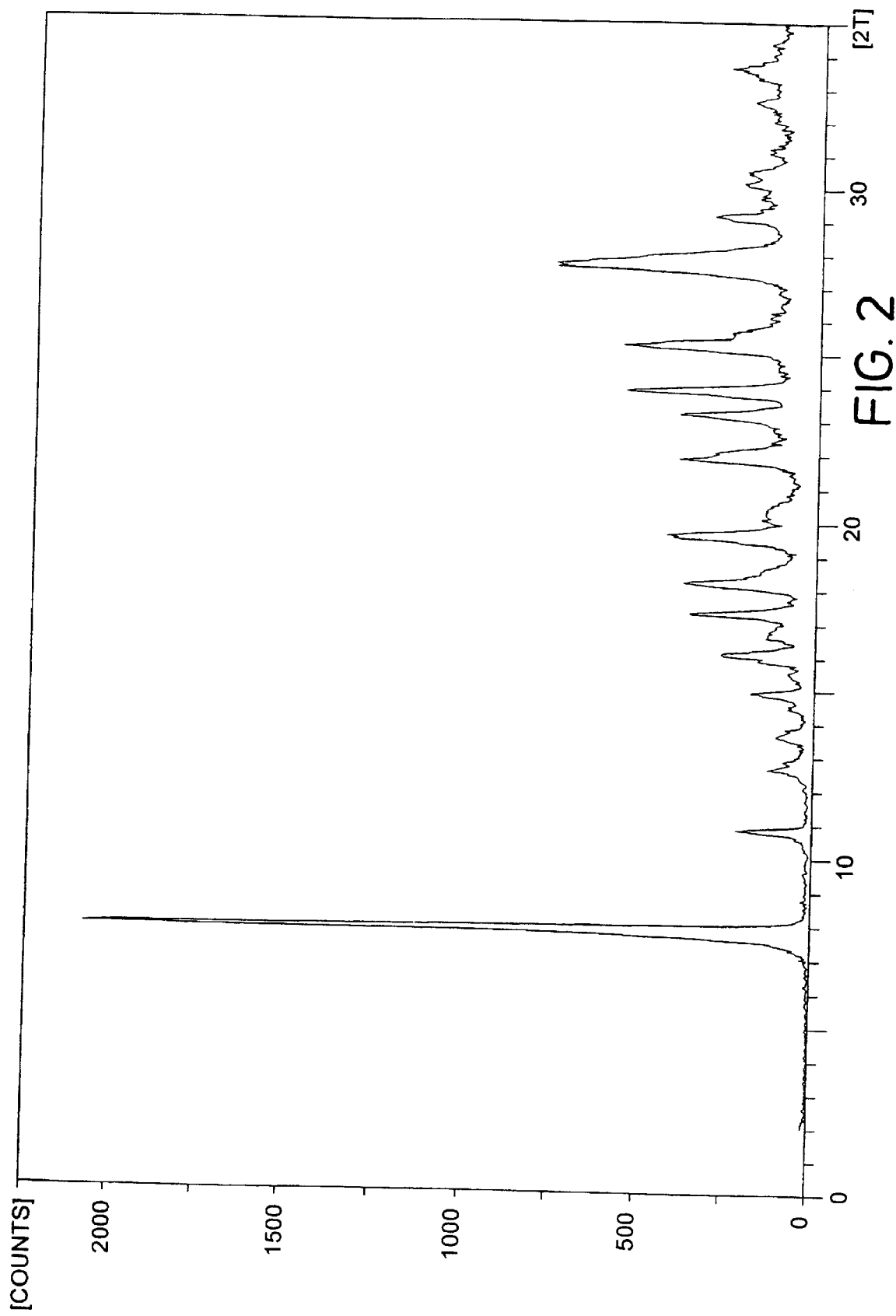
FIG. 2. X-ray powder diffraction pattern of Form II of the compound of formula (I). This pattern was obtained in accordance with the procedures set forth in Example 22.

The X-ray powder diffraction pattern of the product of Example 7 is shown in FIG. 2.

EXAMPLE 8

5,6,-Dichloro-2-(isopropylamino)-1-β-L-ribofuranosyl-1H-benzimidazole Form II

The compound of formula (I) (1.0 wt) was dissolved in ethyl acetate (6.0 vol) and subjected to a finishing filtration. The filtrates were concentrated to approximately 3 volumes. Assuming complete solvent exchange, the solution was reconstituted to 3.5 volumes with methanol. Water (0.5 vol) was added and the solution was cooled to 0–5° C. The crystallization was seeded with a small amount of the pure compound of formula (I) and the solution was stored at 0–5° C. for 2 h. The product was filtered (no wash) and dried in vacuo for 24–48 h at ambient temperature. A second crop was obtained by evaporation of the filtrate to half volume followed by cooling, seeding, and crystallization in a similar manner as above.

The X-ray powder diffraction pattern of the product of Example 8 is shown in FIG. 2.

EXAMPLE 9

5,6,-Dichloro-2-(isopropylamino)-1-β-L-ribofuranosyl-1H-benzimidazole Form II

The compound of formula (I) (10 g) was dissolved in methanol (20 ml) with heating to 50° C. Water (5 ml) was added and the mixture cooled to 5° C. slowly and was stirred at 5° C. for 1 h. The solid was collected by filtration and dried in vacuo at 20° C. for 15 h and at 40° C. for 4 h to yield the compound of formula (I).

The X-ray powder diffraction pattern of the product of Example 9 is shown in FIG. 2.

EXAMPLE 10

Preparation of mixtures of 5,6,-dichloro-2-(isopropylamino)-1-β-L-ribofuranosyl-1H-benzimidazole forms The compound of formula (I) may be dissolved in 2N hydrochloric acid (60 ml) and stirred for 0.5 h and filtered.

The filtrate was heated to 60° C. and 2N sodium hydroxide (55 ml) was added slowly, maintaining the internal temperature between 60–70° C. during the addition. The mixture was stirred at 65–70° C. for 2 h and then cooled to 20° C. over 2 h. The solid was collected by filtration, washing with water (2×30 ml) and dried in vacuo at 40° C. for 16 h to yield the compound of formula (I) (8.8 g, 88%).

EXAMPLE 11

5,6,-Dichloro-2-(isopropylamino)-1-β-L-ribofuranosyl-1H-benzimidazole ethanolate The compound of formula (I) (1.0 wt) was suspended in ethanol/water (10.0 vol) at 70° C. for 2 h. The ethanol/water (v/v) ratios were as follows: 10/90, 15/85, 20/80, 25/75 and 30/70. The resulting solid white free flowing powder was filtered and air-dried. Ethanol solvate was obtained in similar manner from solutions of ethanol/toluene (ratios 5/95, 10/90, 15/85, 20/80, 25/75, and 30/70).

Recrystallization of the compound of formula (I) from ethanol/water gave an ethanol solvate containing 0.5 moles of ethanol per mole of the compound of formula (I).

Figure 3:
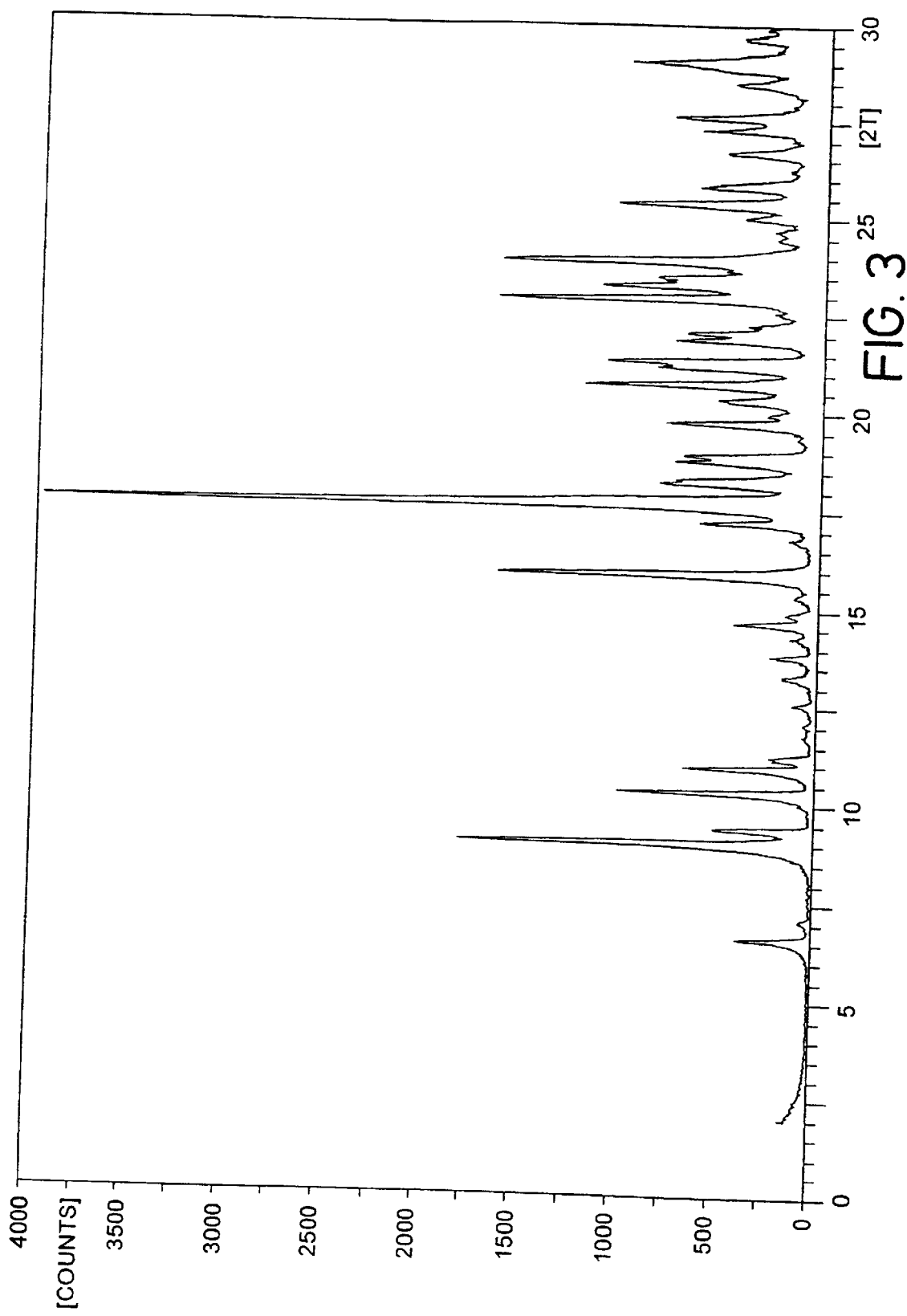
FIG. 3. X-ray powder diffraction pattern of the ethanol solvate of the compound of formula (I) (hereinafter "ethanolate"). This pattern was obtained in accordance with the procedures set forth in Example 22.

The X-ray powder diffraction pattern of the product of Example 11 is shown in FIG. 3.

EXAMPLE 12

5,6,-Dichloro-2-(isopropylamino)-1-β-L-ribofuranosyl-1H-benzimidazole ethanolate The compound of formula (I) (20 g) was added to stirred toluene/ethanol (7:1, 200 ml) and heated to reflux (81° C.) to give a clear solution. The solution was cooled to 20° C. and crystallization occurred at approximately 50° C. The suspension was cooled to 0–5° C. and aged for 2 h. The solid was collected by filtration, and washed with toluene (2×20 ml). The wet cake was dried in vacuo at 40° C.

Recrystallization of the compound of formula (I) from ethanol/toluene gave an ethanol solvate containing 0.5 moles of ethanol per mole of the compound of formula (I).

The X-ray powder diffraction pattern of the product of Example 12 is shown in FIG. 3.

EXAMPLE 13

5,6,-Dichloro-2-(isopropylamino)-1-β-L-ribofuranosyl-1H-benzimidazole Form IV

Water (300 ml) was added to Form I (4 g) as prepared in Example 1 above and stirred for 20 min. The mixture was then heated at 50° C. for 6 days, and then cooled to room temperature. The solid, grainy crystalline material was filtered and dried in vacuo at 60° C.

Figure 4:
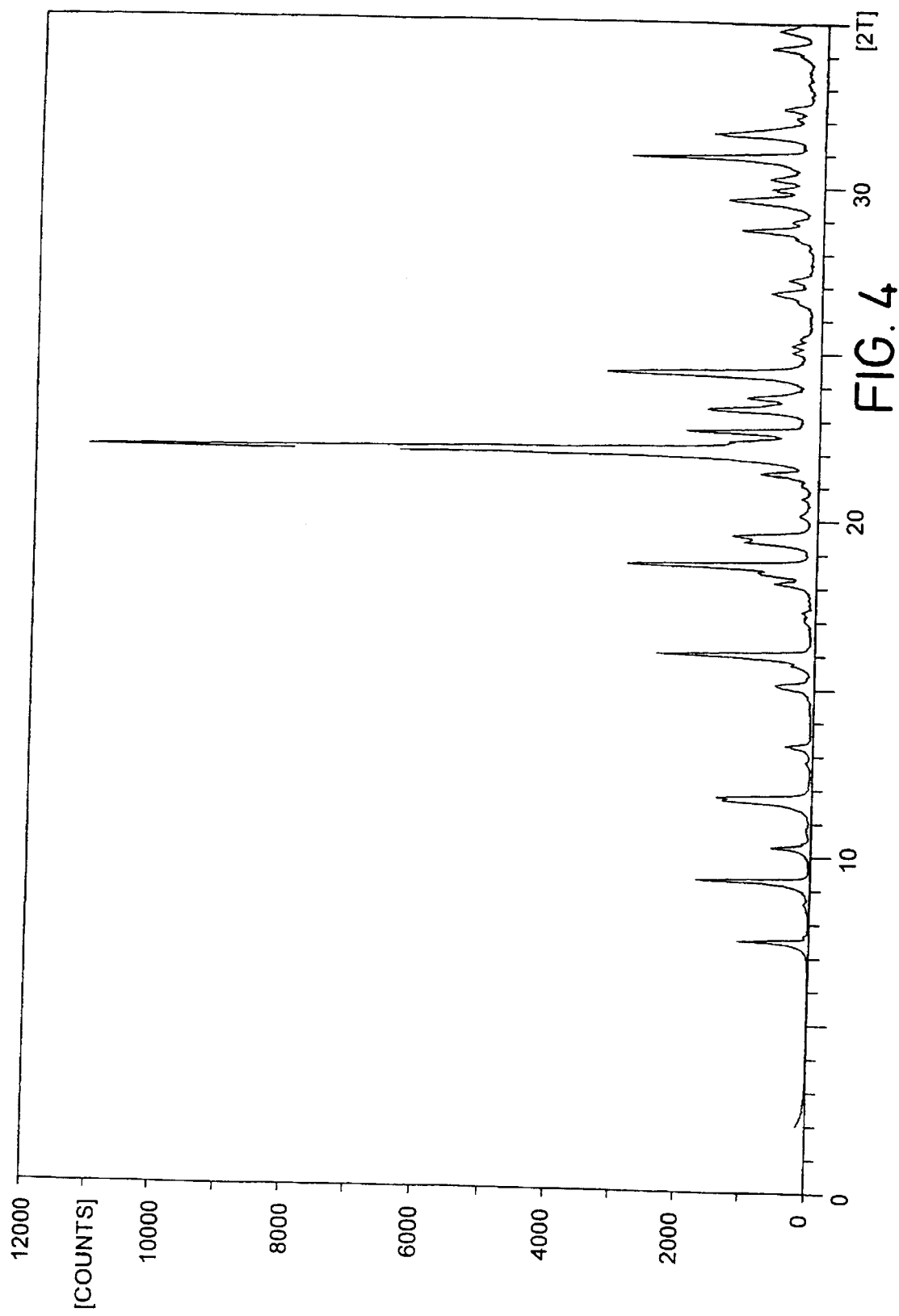
FIG. 4. X-ray powder diffraction pattern of Form IV of the compound of formula (I). This pattern was obtained in accordance with the procedures set forth in Example 22.

The X-ray powder diffraction pattern of the product of Example 13 is shown in FIG. 4.

EXAMPLE 14

5,6,-Dichloro-2-(isopropylamino)-1-β-L-ribofuranosyl-1H-benzimidazole Form V

The compound of formula (I) (2.0 g) was added gradually to water (40 ml) at 70° C. with rapid stirring over 2 h. After heating at 65–70° C. with stirring for an additional 7 h, the heating and stirring were discontinued. After sitting for 2.5 days at ambient temperature, the mixture was filtered. the grainy white solid residue was allowed to air dry overnight affording the compound of formula (I) Form V.

Figure 5:
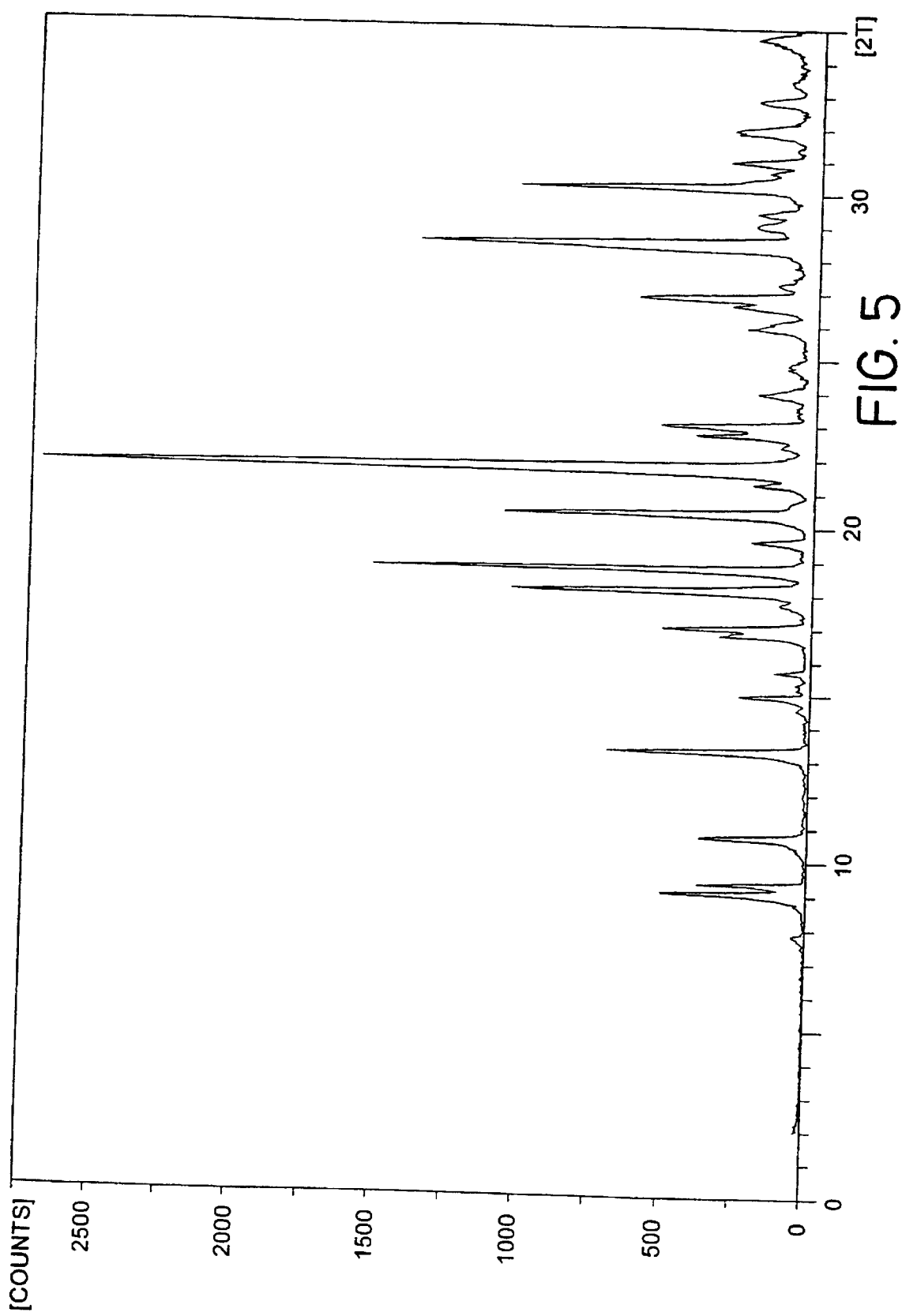
FIG. 5. X-ray powder diffraction pattern of Form V of the compound of formula (I). This pattern was obtained in accordance with the procedures set forth in Example 22.

The X-ray powder diffraction pattern of the product of Example 14 is shown in FIG. 5.

EXAMPLE 15

5,6,-Dichloro-2-(isopropylamino)-1-β-L-ribofuranosyl-1H-benzimidazole Form VI

The compound of formula (I) ethanolate (200 mg) was weighed into small vials. Hydrostats with NaCl saturated solutions and excess NaCl solid were inserted inside the vials. The vials were then sealed very well and stored at 80° C. The samples were removed from the vial and heated to 170° C. on a differential scanning calorimeter and subsequently cooled to room temperature. The powder was collected from DSC pans and analyzed by X-ray diffraction.

Figure 9:
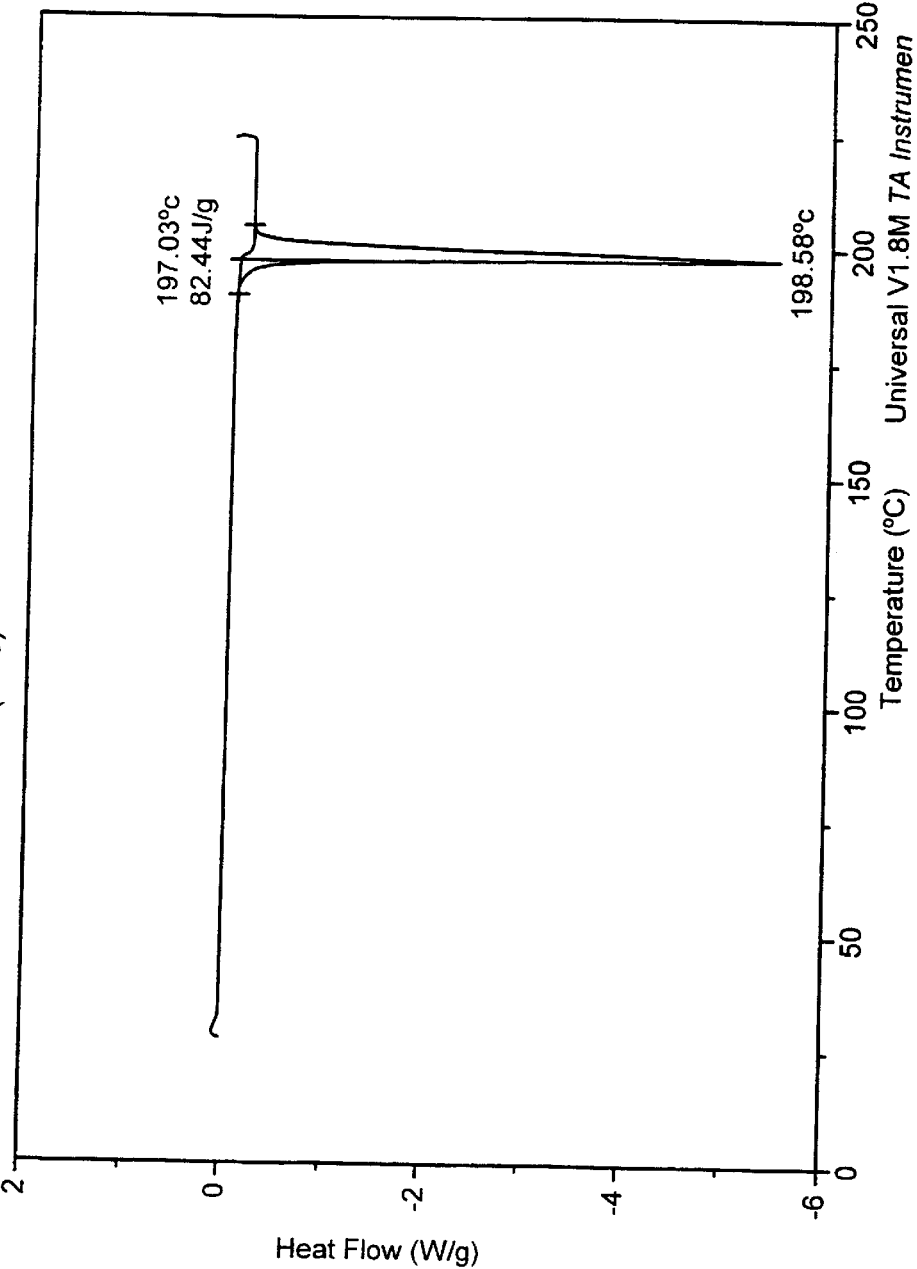
FIG. 9. DSC Thermogram for Form VI of the compound of formula (I). This TGA thermogram was obtained in accordance with the procedures set forth in Example 22.

Characterization: The X-ray powder diffraction pattern of the product of Example 15 (Form VI) is shown in FIG. 6. DSC thermogram for Form VI is illustrated in FIG. 9. The TGA thermogram for Form VI is illustrated in FIG. 7. The moisture sorption isotherm for form VI is shown in FIG. 8.

EXAMPLE 16

Conversion of 5,6-Dichloro-2-(isopropylamino)-1-(beta-L-ribofuranosyl)-1H-benzimidazole Form II to Form VI About 200 mg of Form II seeded with 5 mg of Form VI were suspended in 1 mL of distilled water and stirred in a water bath at 45° C. After 28 hours stirring, the solid was examined with X-ray diffraction. The results from X-ray diffraction suggested that Form II had been converted to form VI completely.

Characterization: as for Example 15.

EXAMPLE 17

Conversion of 5,6-Dichloro-2-(isopropylamino)-1-(beta-L-ribofuranosyl)-1H-benzimidazole ethanol solvate to Form VI About 200 mg of ethanolate seeded with 5 mg of Form VI were suspended in 1 mL of distilled water and stirred in a water bath at 45° C. After 28 hours stirring, the solid was examined with X-ray diffraction. The results from X-ray diffraction suggested that the compound of formula (I) ethanol solvate had been converted to Form VI completely.

Characterization: as for Example 15.

EXAMPLE 18

Conversion of 5,6-Dichloro-2-(isopropylamino)-1-(beta-L-ribofuranosyl)-1H-benzimidazole ethanol solvate to Form VI Ten grams of ethanolate seeded with 100 mg of form VI made from the above conversion study were suspended in 50 mL of distilled water at 45° C. After 5 hours, all ethanolate converted to form VI, as determined by X-ray diffraction examination. The solid was collected by filtration, washing with water (3×5 mL) and dried in a vacuum oven at 100° C. for 3 hours.

Characterization: as for Example 15.

EXAMPLE 19

Conversion of 5,6-dichloro-2-(isopropylamino)-1-(beta-L-ribofuranosyl)-1H-benzimidazole ethanol solvate to Form VI The stability samples of ethanolate stored at 80° C./50% relative humidity (RH), 60° C./75% RH, 60° C./50% RH, and 40° C./75% RH under sealed conditions for 2 months also partially or completely converted to Form VI.

Characterization: as for Example 15.

EXAMPLE 20

Preparation of 5,6-dichloro-2-(isopropylamino)-1-(beta-L-ribofuranosyl)-1H-benzimidazole Form VI by seeding A solution of 5,6-dichloro-2-(isopropylamino)-1-(beta-L-ribofuranosyl)-1H-benzimidazole (10 g) in ethyl acetate (25 ml) and toluene (30 ml) was seeded with 5,6-dichloro-2-(isopropylamino)-1-(beta-L-ribofuranosyl)-1H-benzimidazole Form VI (100 mg). The mixture was heated to 50° C. for 3 h forming a suspension. Further toluene (70 ml) was added over 30 minutes. The suspension was cooled to 25° C. and aged at 25° C. for 2 h. The solid was collected by filtration, washing with ethyl acetate/toluene (1:4, 20 ml). The solid was dried in vacuo at 40° C. to yield 5,6-dichloro-2-(isopropylamino)-1-(beta-L-ribofuranosyl)-1H-benzimidazole Form VI.

Characterization: as for Example 15.

EXAMPLE 21

Preparation of 5,6-dichloro-2-(isopropylamino)-1-(beta-L-ribofuranosyl)-1H-benzimidazole Form VI by Recrystallization from Ethyl Acetate/Toluene Sodium hydroxide (2M, 1790 ml) was added to a slurry of 5,6-dichloro-2-(isopropylamino)-1-(2,3,5-tri-O-acetyl-beta-L-ribofuranosyl)-1H-benzimidazole (358 g) in TMBE (1790 ml) containing methanol (179 ml). The mixture was stirred at 25–30° C. until the reaction was complete. The layers were separated and the aqueous layer further extracted with TBME (716 ml) The combined organic solutions were washed with 10% brine (2×1790 ml). The organic solution was concentrated at atmospheric pressure to about 2.5 vol (895 ml). Ethyl acetate (2864 ml) was added and the solution was again concentrated to about 2.5 vol. The solution was cooled to 40–50° C., and the resulting solution was clarified, rinsing with an ethyl acetate (716 ml) line wash. The clarified solution was concentrated at atmospheric pressure to about 3.3 vol (1180 ml).

The solution was heated to 60° C. Toluene (3000 ml) was heated to 60° C. and added over 1 h to the ethyl acetate solution. The resulting mixture was aged at 60° C. overnight before cooling to 0–5° C. over 1 h then aging at 0.5° C. for about 2 h. The slurry was filtered, washed with ethyl acetate:toluene 1:4 (2×716 ml) and dried in vacuo at 40° C. for 18 h to yield 5,6-dichloro-2-(isopropylamino)-1-(beta-L-ribofuranosyl)-1H-benzimidazole Form VI.

Characterization: as for Example 15.

EXAMPLE 22

Experimental Methods for Form VI Characterization

Differential Scanning Calorimetry and Thermogravimetric Analyzer

Differential scanning calorimetry (DSC) was performed on a TA Instruments DSC 2920 Differential Scanning Calorimetor equipped with a DSC auto sampler. Samples of 1 to 3 mg were crimped in standard aluminum pans with holes and heated from 25° C. to 250° C. at a rate of 10° C./minute under nitrogen purge. The percentage of total weight loss of the drug substance was determined on a TA Instruments Hi-Res TGA 2950 thermogravimetric analyzer (TGA) with a nitrogen purge.

X-Ray Powder Diffraction

The X-ray powder diffraction patterns were determined on a Philips X'Pert MPD diffractometer equipped with diffracted beam graphite monochromator using copper Kα X-radiation and an automated divergent slit. The diffractometer was run in the step scan mode at 0.04° per step and a 1 second count per step. A xenon proportional counter with a graphite monochromator was used as the detector. Samples were back filled into a 16 mm diameter holder having a thickness of about 2.0 mm. The X-ray Powder Diffraction Patterns of Forms I, II, IV, V, VI, and the ethanolate are provided in FIGS. 1, 2, 4, 5, 6, and 3, respectively. The following data, measured in 2 theta angles, d-spacings, relative intensities, and Miller indices were obtained:

TABLE 1

| X-ray Powder Diffraction of Form VI of 1263W94 | | | | | |
|---|---|---|---|---|---|
| 2 θ (°)[1] | Å[2] | I | h[3] | k[3] | l[3] |
| 8.53 | 10.36 | 14.5 | 0 | 0 | 4 |
| 10.47 | 8.45 | 25.6 | 1 | 0 | 2 |
| 12.80 | 6.91 | 16.8 | 0 | 0 | 6 |
| 14.16 | 6.25 | 16.4 | 1 | 1 | 2 |
| 13.51 | 6.55 | 21.4 | 1 | 1 | 0 |
| 14.95 | 5.92 | 60.4 | 1 | 1 | 3 |
| 15.98 | 5.54 | 26.2 | 1 | 1 | 4 |
| 17.23 | 5.14 | 100.0 | 1 | 1 | 5 |
| 19.25 | 4.61 | 19.3 | 2 | 0 | 1 |
| 21.41 | 4.15 | 26.5 | 2 | 1 | 0 |
| 21.83 | 4.07 | 60.4 | 2 | 1 | 2 |
| 22.35 | 3.97 | 38.3 | 2 | 1 | 3 |
| 23.07 | 3.85 | 48.7 | 2 | 1 | 4 |
| 27.49 | 3.24 | 30.9 | 2 | 1 | 8 |
| 30.11 | 2.97 | 18.5 | 2 | 2 | 6 |

[1]Margin of error is approx. ±0.05 degrees.
[2]Margin of error is approx. ±0.05 Å.
[3]The Miller indices, h, k, and l above are used to define uniquely a set of parallel planes in the crystal.

Moisture Sorption

Moisture adsorption/desorption studies were conducted on a VTI vacuum microbalance at 25° C. after drying the sample at 60° C. under vacuum. Moisture adsorption was monitored under vacuum from 0 to 95% relative humidity and desorption was monitored from 95% down to 5% relative humidity. The criteria for equilibrium at a given relative humidity was less than 3 μg of weight change in 18 minutes.

Single Crystal X-ray Diffraction

The crystal structure of a single crystal of Form VI 5,6-dichloro-2-(isopropylamino)-1-(β-L-ribofuranosyl)-1H-benzimidazole was determined using single crystal X-ray diffraction. Single crystal X-ray diffraction data was determined on a Bruker AXS SMART diffractometer equipped with a diffracted beam graphite monochromator using molybdenum Kα X-radiation (lambda=0.71071A) at 160K. The unit cell parameters and space group were determined to be tetragonal crystal system, P4(3)2(1)2, with a=b= 9.1542, c=41.687 (a, b, c units in angstroms), and alpha= beta=gamma=90 degrees. The unit cell parameters at ambient conditions, a=b=9.2794, c=41.593 (a, b, c units in angstroms), and alpha=beta=gamma=90.000 degrees, were calculated by indexing the experimental X-ray powder pattern.

Figure 10:
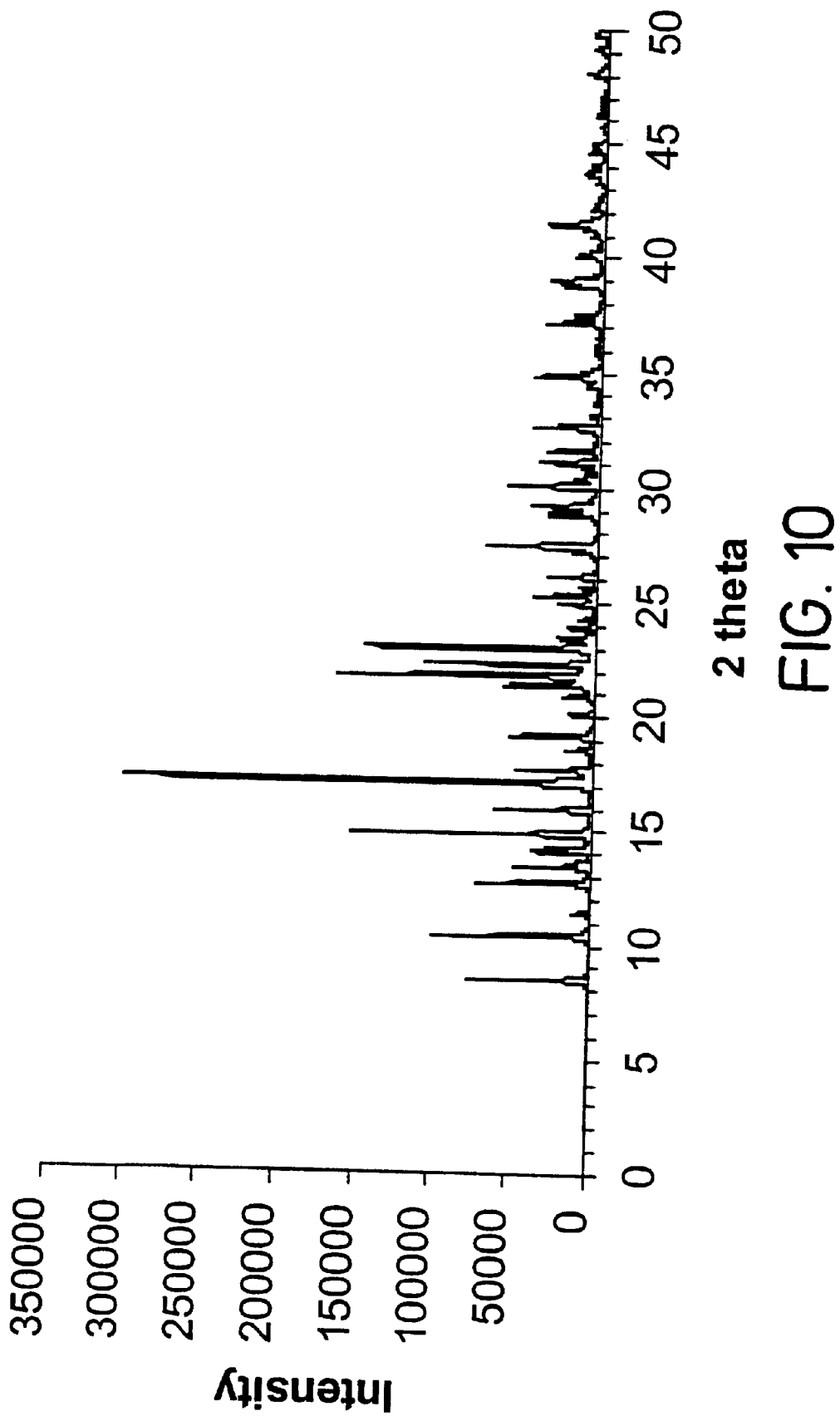
FIG. 10. Single Crystal X-Ray Diffraction Pattern for a single crystal of Form VI of the compound of formula (I). This pattern was obtained in accordance with the procedures set forth in Example 22.

Using the atomic coordinates of the single crystal data and unit cell parameters from indexing the experimental powder pattern, a theoretical X-ray powder diffraction pattern was calculated. The X-ray diffraction pattern for a single crystal of Form VI of 1263W94 is provided in FIG. 10. The 15 most intense peaks from 2 to 35 two theta are presented below in terms of 2 theta angles, d-spacing, relative intensity, and Miller indices.

TABLE 2

Calculated Powder X-ray Diffraction Pattern Based Upon Single Crystal X-ray Diffraction of Form VI of 1263W94

| 2 θ (°)[1] | Å[2] | I | h[3] | k[3] | l[3] |
|---|---|---|---|---|---|
| 17.21 | 5.15 | 100.0 | 1 | 1 | 5 |
| 21.82 | 4.07 | 57.4 | 2 | 1 | 2 |
| 23.06 | 3.85 | 53.2 | 2 | 1 | 4 |
| 14.93 | 5.93 | 51.4 | 1 | 1 | 3 |
| 22.34 | 3.98 | 39.9 | 2 | 1 | 3 |
| 10.43 | 8.47 | 29.2 | 1 | 0 | 2 |
| 12.78 | 6.92 | 22.2 | 1 | 0 | 4 |
| 8.50 | 10.40 | 21.3 | 0 | 0 | 4 |
| 15.96 | 5.55 | 19.2 | 1 | 1 | 4 |
| 30.11 | 2.97 | 17.8 | 2 | 2 | 6 |
| 32.61 | 2.74 | 17.7 | 3 | 0 | 7 |
| 19.23 | 4.61 | 17.6 | 2 | 0 | 1 |
| 21.39 | 4.15 | 17.1 | 2 | 1 | 0 |
| 17.71 | 5.00 | 15.5 | 1 | 0 | 7 |
| 13.48 | 6.56 | 15.5 | 1 | 1 | 0 |

[1] Margin of error is ±0.05 degrees.
[2] Margin of error is ±0.05 Å.
[3] The Miller indices, h, k, and l above are used to define uniquely a set of parallel planes in the crystal.

The 2 theta values derived from single crystal data shown in the graph differ from the observed experimental powder diffraction values reported above primarily due to sample preparation errors, such as sample displacement error, minor errors in diffractometer alignment, and variation in method of peak determination by computer. The relative intensity of the peaks in the calculated pattern is affected not only by the input single crystal data but also by the peak profile (shape and broadening) used in the calculation of the simulated powder pattern.

EXAMPLE 23

Tablet Formulation

The following formulations were prepared as follows using the compound of formula (I) Form VI.

Formulation A
1263W94 Tablets (form VI)

| Direct Compression Potency | 100 mg | 400 mg |
|---|---|---|
| Core Ingredients | | |
| 1263W94 (active) | 100.0[2] | 400.0[3] |
| Microcrystalline Cellulose, NF | 93.5 | 374.0 |
| Crospovidone, NF | 4.0 | 16.0 |
| Colloidal Silicon Dioxide, NF | — | 0.4 |
| Magnesium Stearate, NF | 2.5 | 10.0 |
| Total (core) | 200.0 mg | 800.4 mg |
| Coating Ingredients | | |
| Opadry White YS-1-18034 | 6.0 | 24.0 |
| Purified Water USP[1] | QS | QS |
| Total (core) | 206.0 mg | 824.4 mg |
| Theoretical Batch Size (cores) | | |
| kg | 15.0 | 33.0 |
| tablets | 75000 | 41254 |

[1] Removed during processing
[2] Equivalent to 100 mg of 1263W94 per tablet
[3] Equivalent to 400 mg of 1263W94 per tablet

Manufacturing Procedure for Direct Compression

All ingredients were screened, except the magnesium stearate, using 20 or 30 mesh. All ingredients were blended, excluding the magnesium stearate, until uniform. The magnesium stearate was screened as above. The magnesium stearate was added to the other ingredients and blended. The tablets were compressed using a rotary press.

A 10% coating suspension was prepared by mixing Opadry with water. Tablets were coated to a weight gain of approximately 3%.

Formulation B
1263W94 Tablets (form VI)

| Wet Granulation Potency | 100 mg | 400 mg |
|---|---|---|
| Core Ingredients | | |
| 1263W94 (active) | 102.0[2] | 408.0[3] |
| Lactose, anhydrous, NF | 60.0 | 240.0 |
| Microcrystalline Cellulose, NF | 20.0 | 80.0 |
| Crospovidone, NF | 15.0 | 60.0 |
| Povidone, USP, K30 | 7.5 | 30.0 |
| Magnesium Stearate, NF | 0.6 | 2.4 |
| Purified Water USP[1] | QS | QS |
| Total (core) | 205.1 mg | 816.0 mg |
| Coating Ingredients | | |
| Opadry White YS-1-18034 | 6.0 | 24.0 |
| Purified Water USP[1] | QS | QS |
| Total (core) | 211.1 mg | 840.0 mg |
| Theoretical Batch Size (cores) | | |
| kg | 0.718 | |
| tablets | 3500 | |

[1] Removed during processing
[2] Equivalent to 100 mg of 1263W94 per tablet
[3] Equivalent to 400 mg of 1263W94 per tablet Formulation B-1
1263W94 Tablets (form VI)

| Wet Granulation Potency | 400 mg |
|---|---|
| Core Ingredients | |
| 1263W94 (active) | 400[2] |
| Microcrystalline Cellulose | 298.0 |
| Lactose, Hydrous | 60.0 |
| Crospovidone, NF | 24.0 |
| Povidone, USP | 12.0 |
| Magnesium Stearate, NF | 2.0 |
| Purified Water USP[1] | QS |
| Total (core) | 816.0 mg |
| Coating Ingredients | |
| Opadry White YS-1-18034 | 24.0 |
| Purified Water USP[1] | QS |
| Total (core) | 820.0 mg |

[1] Removed during processing
[2] Equivalent to 400 mg of 1263W94 per tablet

Manufacturing Procedure for Wet Granulation

The granule ingredients were screened using a 20 or 30 mesh. The granule ingredients were dry blended in a high shear granulator until uniform and then granulated in a high shear granulator using purified water. The granule was dried to a loss on drying of less than 2%. The granule was screened as above. The remaining ingredients were screened as above. The granule was blended with the remaining ingredients. The tablets were compressed using a rotary press. A 10% coating suspension was prepared by mixing Opadry with water. Tablets were coated to a weight gain of approximately 3%.

EXAMPLE 24

Capsule Formulation

The following formulation may be prepared as follows using the compound of formula (I) Form VI.

| 1263W94 Capsules (form VI) | |
|---|---|
| Potency | 100 mg |
| Capsule Fill Ingredients | |
| 1263W94 (active) | 101.0[1] |
| Lactose, Anhydrous NF | 232.0 |
| Crospovidone, NF | 17.0 |
| Magnesium Stearate, NF | 1.0 |
| Total Fill Weight | 351.0 mg |
| Capsule Shell | |
| Gelatin, white opaque cap and body | 81.1 |
| Total Weight | 432.5 mg |

[1]Equivalent to 100 mg of 1263W94 per tablet.

Manufacturing Procedure for Capsules

The capsule fill ingredients are mixed using a mortar and pestle by geometric dilution. The combined capsule fill ingredients are filled into the gelatin capsules by hand. Capsules are closed by hand.

EXAMPLE 25

Oral Solution Formulation

The following formulation was prepared as follows using the compound of formula (I) Form VI.

| 1263W94 Oral Solution (Prepared using Form VI) | |
|---|---|
| Potency | 30 mg/ml |
| Ingredients | per 100 ml |
| 1263W94 | 3.0 g |
| Citric Acid, Anhydrous | 0.3 g |
| Hydrochloric Acid 1 N | 6.9 ml |
| Propylene Glycol USP | 20.0 ml |
| Purified Water USP | 20.0 ml |
| Hydrochloric Acid 1 N | QS |
| Sorbitol Solution (60% w/v) | 50.0 ml |
| Purified Water USP | QS |
| Total Volume | 100.0 ml |

Manufacturing Procedure for Oral Solution

Propylene glycol, water and hydrochloric acid (6.9 ml) were combined and mixed to uniformity. Citric acid was added and the mixture was stirred until the citric acid dissolved. The active was added and dissolved by mixing. If necessary, pH can be adjusted to between 2.0 and 2.5 by adding 1N hydrochloric acid solution or 1N sodium hydroxide solution. Thereafter the sorbitol solution was added and mixed to uniformity. The final volume was adjusted to 100 ml by addition of purified water.

EXAMPLE 26

Oral Suspension Formulation

The following formulation may be prepared as follows using the compound of formula (I) Form VI.

| 1263W94 Oral Suspension (Form VI) | |
|---|---|
| Potency | 30 mg/ml |
| Ingredients | per 100 ml |
| 1263W94 (active) | 3.0 g |
| Sucrose | 50.0 g |
| Propylene Glycol | 5.0 g |
| Sodium Chloride | 0.5 g |
| Citric Acid | QS |
| Sodium Citrate | QS |
| Microcrystalline Cellulose and Sodium Carboxymethylcellulose | 2.5 g |
| Sodium Carboxymethylcellulose | 0.25 g |
| Polysorbate 80 | 0.2 g |
| Sodium Benzoate | 0.1 g |
| Methylparaben | 0.1 g |
| Flavorant | 0.2 ml |
| Colorant | 0.005 g |
| Purified Water USP | QS |
| Total Volume | 100.0 ml |

Manufacturing Procedure for Oral Solution

Sucrose is dissolved in purified water to approximately 70% of total batch volume. While mixing continuously, sodium chloride, citric acid, sodium citrate, and sodium benzoate are added and dissovled. If necessary, the pH is adjusted to between 5.0 and 6.0, by adding sufficient citric acid or sodium citrate as necessary. Microcrystalline cellulose and sodium carboxymethylcellulose (Avicel RC 591) are added while mixing and mixing is continued until a uniform, smooth dispersion is formed. Polysorbate 80 is added while mixing. In a separate vessel, methylparaben is dissolved in propylene glycol and sodium carboxy methyl cellulose (0.25 g) is dispersed, and this liquid is added to the bulk dispersion while mixing. The active ingredient is gradually dispersed in the bulk liquid while mixing continuously, to produce a uniform dispersion. Flavorant and Colorant are added and the volume is adjusted to 100 ml by addition of purified water. The suspension is then homogenized by passing through a pump and a colloid mill.

The foregoing Examples are illustrative of the present invention and are not to be construed as limiting thereof. The invention is defined by the following claims including equivalents thereof.

What is claimed is:

1. Form VI 5,6-dichloro-2-(isopropylamino)-1-β-L-ribofuranosyl-1H-benzimidazole characterized by an X-ray powder diffraction pattern expressed in terms of 2 theta angles and obtained with a diffractometer equipped with a diffracted beam graphite monochromator using copper Kα X-radiation, said X-ray powder diffraction pattern comprising 2 theta angle at 8.53±0.05 degrees.

2. A pharmaceutical composition comprising a crystalline form of a compound as claimed in claim 1 and at least one pharmaceutically acceptable carrier therefor.

3. A pharmaceutical composition according to claim 2 in the form of a powder.

4. A pharmaceutical composition according to claim 2 in the form of a tablet.

5. A pharmaceutical composition according to claim 2 in the form of a capsule.

6. A pharmaceutical composition according to claim 2 in the form of a suspension.

7. A method for the treatment of prophylaxis of a herpes viral infection in a human which comprises administering to the human, an effective antiviral amount of crystalline 5,6-dichloro-2-(isopropylamino)-1-β-L-ribofuranosyl-1H-benzimidazole as claimed in claim 1.

8. The method according to claim 7, wherein said herpes viral infection is cytomegalovirus (CMV).

9. A process for the production of 5,6-dichloro-2-(isopropylamino)-1-β-L-ribofuranosyl-1H-benzimidazole as claimed in claim 1 comprising the addition of Form VI 5,6-dichloro-2-(isopropylamino)-1-β-L-ribofuranosyl-1H-benzimidazole to an aqueous suspension of Form II or to an aqueous suspension of the ethanol solvate of 5,6-dichloro-2-(isopropylamino)-1-β-L-ribofuranosyl-1H-benzimidazole.

10. A process for the production of 5,6-dichloro-2-(isopropylamino)-1-β-L-ribofuranosyl-1H-benzimidazole as claimed in claim 1 said process comprising crystallization of 5,6-dichloro-2-(isopropylamino)-1-β-L-ribofuranosyl-1H-benzimidazole from a solution of ethyl acetate and toluene.

11. Form VI 5,6-dichloro-2-(isopropylamino)-1-β-L-ribofuranosyl-1H-benzimidazole having substantially the same X-ray powder diffraction pattern as FIG. 6, wherein said X-ray powder diffraction pattern is obtained with a diffractometer equipped with a diffracted beam graphite monochromator using copper Kα X-radiation.

12. A crystalline form of 5,6-dichloro-2-(isopropylamino)-1-β-L-ribofuranosyl-1H-benzimidazole characterized by an X-ray powder diffraction pattern expressed in terms of 2 theta angles and obtained with a diffractometer equipped with a diffracted beam graphite monochromator using copper Kα X-radiation, wherein said X-ray powder diffraction pattern comprises 2 theta angles at five or more positions selected from the group consisting of 8.53±0.05, 10.47±0.05, 13.51±0.05, 14.95±0.05, 15.98±0.05, 17.23±0.05, 21.41±0.05, 21.83±0.05, 22.35±0.05, 23.07±0.05, and 27.49±0.05 degrees.

13. A crystalline form of 5,6-dichloro-2-(isopropylamino)-1-β-L-ribofuranosyl-1H-benzimidazole characterized by an X-ray powder diffraction pattern expressed in terms of 2 theta angles and relative peak intensities (I) and obtained with a diffractometer equipped with a diffracted beam graphite monochromator using copper Kα X-radiation:

| 2 theta angle (°) | I |
|---|---|
| 8.53 ± 0.05 | 14.5 |
| 10.47 ± 0.05 | 25.6 |
| 12.80 ± 0.05 | 16.8 |
| 14.16 ± 0.05 | 16.4 |
| 13.51 ± 0.05 | 21.4 |
| 14.95 ± 0.05 | 60.4 |
| 15.98 ± 0.05 | 26.2 |
| 17.23 ± 0.05 | 100.0 |
| 19.25 ± 0.05 | 19.3 |
| 21.41 ± 0.05 | 26.5 |
| 21.83 ± 0.05 | 60.4 |
| 22.35 ± 0.05 | 38.3 |
| 23.07 ± 0.05 | 48.7 |
| 27.49 ± 0.05 | 30.9 |
| 30.11 ± 0.05 | 18.5. |

14. A composition comprising Form VI 5,6-dichloro-2-(isopropylamino)-1-β-L-ribofuranosyl-1H-benzimidazole according to claim 1 and amorphous 5,6-dichloro-2-(isopropylamino)-1-β-L-ribofuranosyl-1H-benzimidazole.

15. A process for the production 5,6-dichloro-2-(isopropylamino)-1-β-L-ribofuranosyl-1H-benzimidozole in anhydrous crystalline form VI, said process comprising the steps of:

a) providing 5,6-dichloro-2-(isopropylamino)-1-β-L-ribofuranosyl-1H-benzimidazole in solution either in free base or salt form;

b) isolating 5,6-dichloro-2-(isopropylamino)-1-β-L-ribofuranosyl-1H-benzimidazole from the solution and optionally removing unbound solvent leaving the 5,-dichloro-2-(isopropylamino)-1-β-L-ribofuranosyl-1H-benzimidazole in substantially dry form;

c) treating 5,6-dichloro-2-(isopropylamino)-1-β-L-ribofuranosyl-1H-benzimidazole with a solubilising solvent serving to convert an amount of said optionally dried 5,6-dichloro-2-(isopropylamino)-1-β-L-ribofuranosyl-1H-benzimidazole into said 5,6-dichloro-2-(isopropylamino)-1-β-L-ribofuranosyl-1H-benzimidazole anhydrous crystalline form VI; and d) isolating said anhydrous crystalline form VI.

* * * * *